United States Patent [19]
Bloch et al.

[11] Patent Number: 4,789,630
[45] Date of Patent: Dec. 6, 1988

[54] IONIC COMPOUNDS CONTAINING THE CATIONIC MERIQUINONE OF A BENZIDINE

[75] Inventors: Will Bloch, El Cerrito; Patrick J. Sheridan, San Leandro; Robert J. Goodson, Albany, all of Calif.

[73] Assignee: Cetus Corporation, Emeryville, Calif.

[21] Appl. No.: 896,677

[22] Filed: Aug. 20, 1986

Related U.S. Application Data

[63] Continuation-in-part of Ser. No. 784,329, Oct. 4, 1985, abandoned.

[51] Int. Cl.$^4$ ............................................. G01N 33/53
[52] U.S. Cl. ............................................ 435/7; 435/6; 435/28; 435/803; 435/810; 436/501; 260/396 R; 260/396 N; 564/248; 935/78
[58] Field of Search ................... 260/396 R, 396 N; 564/248; 435/7, 28, 810, 6, 803; 436/501; 935/78

[56] References Cited

U.S. PATENT DOCUMENTS 4,447,542  5/1984  Gantzer .
4,525,452  6/1985  Jones et al. .
4,581,333  4/1986  Kourilsky et al. .

OTHER PUBLICATIONS

Holland et al., *Tetrahedron*, 30:3299-3302 (1974).
Garner et al., *Cancer Letters*, 1:39-42 (1975).
Ashby et al., *Progress in Mutation Research*, 1:32-48 (1981).
Purchase et al., *Progress in Mutation Research*, 1:86-95 (1981).
Bos et al., *Journal of Immunoassay*, 2:187-204 (1981).
Liem et al., *Analytical Biochemistry*, 98:388-395 (1979).
Lijana et al., *Journal of Laboratory and Clinical Medicine*, 94:266-276 (1979).
Welch et al., *Clinical Chemistry*, 29:2022-2025 (1983).
Salauze et al., *Annales de Giologie Clinique*, 42:237-239 (1984).
Thomas et al., *Analytical Biochemistry*, 75:168-176 (1976).
Broyles et al., *Analytical Biochemistry*, 94:211-219 (1979).
Francis et al., *Analytical Biochemistry*, 136:509-514 (1984).
Miller and Nicholas, *Analytical Biochemistry*, 140:577-580 (1984).
Mesulam, *Journal of Histochemistry and Cytochemistry*, 26:106-117 (1978).
Morrell et al., *Journal of Histochemistry and Cytochemistry*, 29:903-916 (1981).
Olsson et al., *Journal of Neuroscience Methods*, 7:49-59 (1983).
Gibson et al., *Brain Research*, 298:235-241 (1984).
Fujii et al., *Neuroscience Research*, 1:153-156 (1984).
Hawkes et al., *Analytical Biochemistry*, 119:142-147 (1982).
Hsu et al., *American Journal of Clinical Pathology*, 75:734-738 (1981).
Nakane, *Journal of Histochemistry and Cytochemistry*, 16:557-560 (1968).
Geysen et al., *Electrophoresis*, 5:129-131 (1984).
Graham et al., *Journal of Histochemistry and Cytochemistry*, 13:150-152 (1965).

(List continued on next page.)

Primary Examiner—Robert J. Warden
Assistant Examiner—Stephen C. Wieder
Attorney, Agent, or Firm—Albert P. Halluin; Janet E. Hasak; Dianne E. Reed

[57] ABSTRACT

Useful for visualizing biological materials in a solid phase, on a gel, or in a liquid phase is a solid salt of the meriquinone of benzidine or a substituted benzidine. An immobilized or dissolved complex of a polymeric anion and the meriquinone of benzidine or a substituted benzidine having controllable solubility may also be employed. Preferred are meriquinone salts and complexes of 3,3,5,5'-tetramethylbenzidine. For visualization, the benzidine or substituted benzidine is oxidized to its meriquinone at pH 3 to 7 in the presence of an effective anion or polymeric anion, an oxidation catalyst, and an effective amount of oxidant to form a solid salt or immobilized complex of the meriquinone under conditions where the meriquinone solubility lies below about $10^{-5}$ M.

67 Claims, 3 Drawing Sheets

OTHER PUBLICATIONS

Trojanowski et al., *Journal of Histochemistry and Cytochemistry*, 31:1217–1223 (1983).
Imberty et al., *Plant Science Letters*, 35:103–108 (1984).
Josephy et al., *J. Biol. Chem.*, 257:3668–3675 (1982).
Claiborn and Fridovich, *Biochemistry*, 18:2324–2329 (1979).
Josephy et al., *J. Biol. Chem.*, 258:5561–5569 (1983).
Straus, *Journal of Histochemistry and Cytochemistry*, 12:462–469 (1963).
Adams, *Neuroscience Letters*, 17:7–9 (1980).
Albers et al., *Journal of Histochemistry and Cytochemistry*, 32:1005–1008 (1984).
Weiss, *Chemistry and Industry*, 16, 517–518 (1938).

COUPLED REACTIONS FOR THE TMB OXIDATION / PRECIPITATION SYSTEM

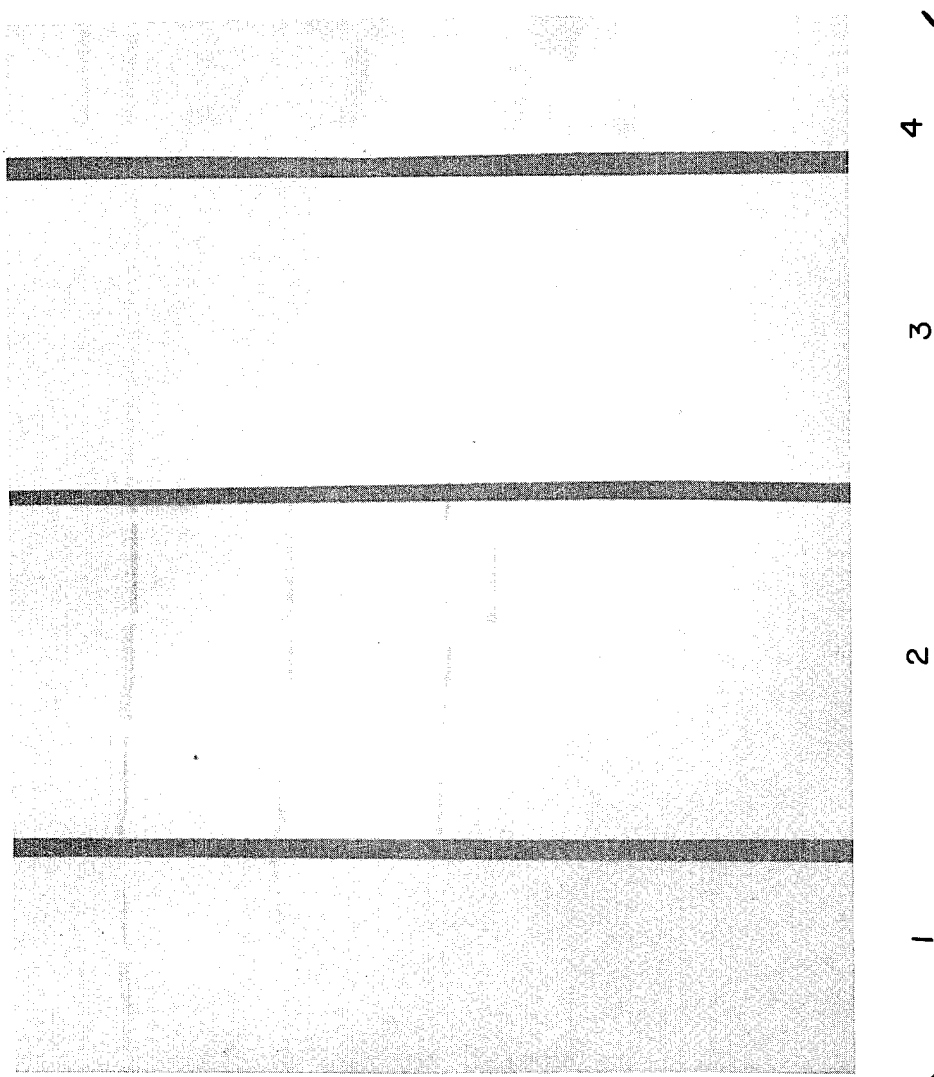

IONIC COMPOUNDS CONTAINING THE CATIONIC MERIQUINONE OF A BENZIDINE

This application is a continuation-in-part of copending U.S. application Ser. No. 784,329 filed Oct. 4, 1985, now abandoned.

BACKGROUND OF THE INVENTION

1. Field of the Invention

This invention relates to novel sparingly soluble salts and immobilized ionic complexes of the meriquinone oxidation products of benzidine and substituted benzidines and to their use as analytical visualization signals in a wide array of chemical, biological and clinical tests.

2. Description of Background and Related Art

Peroxidative oxidation usually occurs according to one or the other of the following reaction schemes: $AH_2 + ROOH \rightarrow A + ROH + H_2O$; $H_2O + AH_2 + ROOH \rightarrow AH_2^{+2} + ROH + 2OH^-$; in which $AH_2$ is a hydrogen donor and ROOH is a hydroperoxide. (Which reaction is preferred depends on the base strength of A and on the reaction pH.) Over the years, many analyses for peroxidative activity have been developed. Some are intended to identify, locate or quantitate peroxides either as compounds of interest or, in the case of hydrogen peroxide, as the product of oxidation by molecular oxygen, especially those catalyzed by a class of enzymes known as oxidases. Other such methods are intended to identify, locate, or quantitate catalysts of peroxidative activity, such as transition-metal ions, hemes, hemoproteins, and the peroxidase enzymes. Among the latter, two classes of use predominate over all others: (a) the analysis of hemoglobin in forensic specimens, feces, urine, and cell-free blood plasma or serum, and (b) the analysis of peroxidase employed as a label in binding assays.

The first class of assays is not very sensitive, because non-peroxidase hemoproteins and isolated hemes are inefficient peroxidative catalysts. Furthermore, they are subject to interference from contaminating transition-metal ions, principally iron and copper, and occasionally from contaminating peroxidase enzymes. Nevertheless, they are so simple and their diagnostic relevance is so great that they are popular in their respective fields of use. For example, many commercial clinical tests for occult blood in fecal material exist for screening for cancer and pre-cancerous growths in the colon.

The second class of assays can be extremely sensitive, because horseradish peroxidase not only is much more efficient catalytically than other hemoproteins, but also is one of the most efficient enzymes capable of producing colored products suitable for spectrophotometric or fluorometric analysis. They also can be highly specific, because peroxidase enzymes occur naturally in relatively few clinical or biological samples, and the potential transition-metal-ion interference usually can be blocked with chelating agents.

A key variable in the design of peroxidase-linked assays is the choice of chromogenic substrate, for several reasons:

(a) Enzyme catalytic efficiency ranges over several orders of magnitude, depending on the structure of the hydrogen donor.

(b) Some spectral changes accompanying oxidation are more sensitive than others, having larger extinction coefficient changes or occuring in more easily detected spectral regions.

(c) Some colored products are soluble; others are insoluble. The former are desirable for instrumental analyses of product absorbance or fluorescence in solution. The latter are essential for assays in which the signal should be localized or trapped in a gel or on a solid surface.

(d) Many peroxidase substrates, phenols and aromatic amines, are known or thought to be mutagenic or carcinogenic.

Benzidine and several substituted benzidine derivatives were developed as peroxidase substrates consumed with higher turnover numbers than many other aromatic amines and phenols, giving convenient and large absorbance changes in the visible spectral region. Most can give water-insoluble products, usually polymeric in nature. However, most are known or thought to be carcinogenic or mutagenic. 3,3',5,5'-tetramethylbenzidine (TMB) was developed as a non-carcinogenic peroxidase substrate (e.g., Holland et al. (1974) *Tetrahedron*, 30: 3299-3302). For this reason, and because it also appears to be one of the most sensitive peroxidase substrates, it has rapidly found widespread use (a) in enzyme immunoassays in which the product color is measured spectrophotometrically in solution (e.g., Bos et al. (1981) *Journal of Immunoassay*, 2: 187-204), (b) in solution-phase spectrophotometric determination of hemoglobin (e.g., Liem et al. (1979) *Analytical Biochemistry*, 98: 388-395), (c) in solid-phase spectrophotometric determination of hemoglobin (e.g., Burkhardt et al. (1981) European Patent Application No. 81104634.1; U.S. Pat. No. 4,447,542) or drugs (via peroxidase-linked specific binding assay, U.S. Pat. No. 4,447,529), (d) in detection of hemoglobin, other hemoproteins, or oxidases in electrophoretic gels (e.g., Thomas et al. (1976) *Analytical Biochemistry*, 75: 168-176), and (e) in neurohistochemistry (e.g., Mesulam (1978) *Journal of Histochemistry and Cytochemistry*, 26: 106-117).

Conspicuously scarce in the documentary record are reports of TMB as a peroxidase substrate in common enzyme-linked solid-phase assays such as immunohistochemical staining, Western blots, Southern blots, or immunodot blots, where less sensitive and more hazardous HRP substrates forming insoluble products have been used (e.g., Hawkes et al. (1982) *Analytical Biochemistry*, 119: 142-147). Although there are no published applications of TMB to Southern, Northern, Western, or immunodot blots, Trojanowski et al. (1983) *Journal of Histochemistry and Cytochemistry*, 31: 1217-1223 reported its immunohistochemical use in a comparison with several other chromogens which clearly form insoluble products: diaminobenzidine, aminoethylcarbazole, o-tolidine, and a mixture of paraphenylene diamine and pyrocatechol. However, TMB was judged to be one of the least effective substrates, being less sensitive than diaminobenzidine (despite the opposite finding in neurohistochemical studies) and giving crystals sufficiently large to obscure microstructural detail.

In several of the other solid-phase or gel-phase studies cited above, the TMB signal was also not completely satisfactory. Fujii et al. (1984) *Neuroscience Research*, 1: 153-156 cited the instability of the TMB product in the absence of special fixatives, and Olsson et al. (1983) *J. Neuroscience Methods*, 7: 49-59 and many other neurohistochemists mentioned the tendency of the TMB product to form crystals so large that they obscured fine detail. In an histochemical effort to observe the localization of native peroxidase in cross-sections of plant stems, the TMB-generated color was observed to be unstable (Imberty et al. (1984) *Plant Science Letters*, 35: 103-108). Broyles et al. (1979) *Analytical Biochemistry*, 94: 211-219 found the TMB product to be mobile in the stained electrophoretic gel, frustrating either quantitation or maintenance of a permanent record. Both Broyles et al. and Francis et al. (1984) *Analytical Biochemistry*, 136: 509-514 noted a colored background in TMB-stained gels which must represent peroxidative catalysis by impurities in the gel or the reagents. In the other cited class of solid-phase assays of hemoglobin or peroxidase (e.g., Burkhardt et al., supra), the assay interval was so short that physical form of liability of the TMB product would be unlikely to influence the outcome.

Removal of two electrons from benzidine or a substituted benzidine (e.g., by peroxidative oxidation) creates an oxidized product called a quinone diimine. The blue reaction product of TMB oxidation has been reported to exist largely as a charge-transfer complex between one TMB molecule and one quinone diimine, having an average oxidation state halfway between those of its two components and called a meriquinone (Josephy et al. (1982) *J. Biol. Chem.*, 257: 3668-3675). In that paper, both the meriquinone and the quinone diimine were represented as neutral molecules, as had also been the case in an earlier paper on the mechanism of ortho-dianisidine oxidation (Claiborn and Fridovich (1979) *Biochemistry*, 18: 2324-2329). Later the quinone diimine and meriquinone formed from benzidine oxidation were drawn as dications (Josephy et al. (1983) *J. Biol. Chem.*, 258: 5561-5569), although no $pK_a$ values for meriquinones or quinone diimines have been reported.

Before the discovery of TMB, Straus (1963) *Journal of Histochemistry and Cytochemistry*, 12: 462-469 observed that unspecified buffer salts caused the blue product of benzidine oxidation (meriquinone) to form crystals of undetermined composition. Other solid-phase or gel-phase applications of TMB as a peroxidative substrate, cited above, used buffers the anions of which (acetate, citrate and phosphate) applicants have shown to form relatively soluble salts of the TMB meriquinone. While Mesulam, supra, Olsson et al., supra, and other neurohistochemists reported the deposition of the blue product of TMB oxidation as crystals (of undetermined composition) from acetate and phosphate buffers in neurohistochemical applications, most of the cited references on solid-phase and gel-phase applications disclose no clear evidence of product precipitation or immobilization. In fact, the opposite result was reported by Broyles et al., supra. As recently as 1983, Josephy et al. (*Journal of Biological Chemistry*, 285: 5561-5569) cited the observation of Broyles et al. regarding unsatisfactory solubility properties of the TMB meriquinone. Neurohistochemists have used methyl salicylate (Adams (1980) *Neuroscience Letters*, 17: 7-9), ammonium molybdate (Fujii et al., supra), potassium ferricyanide (Albers et al. (1984) *Journal of Histochemistry and Cytochemistry*, 32: 1005-1008), or sodium nitroprusside (e.g., Mesulam, supra) to stabilize the blue TMB product. However, the molecular basis of these effects is unknown. Methyl salicylate is non-ionic in the pH range used, and the other three stabilizers can undergo reduction reactions or serve as sources of anions which might precipitate the meriquinone. U.S. Pat. No. 4,525,452 describes the isolation of unoxidized TMB as a solid sulfate or dichloride salt, but no reference is made to oxidized TMB.

The principal reported difficulties in applying TMB as a peroxidative substrate in solid-phase or gel-phase assays are (a) excessive solubility of the colored reaction product, (b) lack of control of crystallization in the neurological and immunohistochemical staining applications where insoluble product is obtained but large crystals can obscure cellular microstructures, (c) excessive background oxidation of TMB by contaminants, and (d) "fading" of the meriquinone color for unspecified reasons.

Van Duijn *Receuil des Travaux Chimiques des Pays-Bas* (1955) 74: 771-778 disclosed that inorganic $Cl^-$ and $SO_4^{-2}$ salts precipitated the blue meriquinone intermediate of benzidine oxidation. The precipitates were not shown to be ionic nor precipitation shown to be complete. In addition, no quantitation of meriquinone solubility was made. Weis *Chemistry and Industry* (1938) 16: 517-518 disclosed nonexperimental suggestions that the blue compounds observed by Schlenk and by Barzilowsky were semiquinones, not charge-transfer complex meriquinones, that the semiquinones should be mono-cations, and that the blue solids obtained with various anions should be salts. Schlenk *Annalen der Chemie* (1908) 363: 313-339 disclosed blue chloride "salts" of the meriquinones of 3,3'-dichloro-5,5'-dimethylbenzidine and 3,3'-dimethylbenzidine precipitated from water. No measurement of solubility or proof of the ionic nature of the solids was obtained. Barzilowsky *Chemikes-Zeitung* (1905) 29: 292 disclosed the salt of ferrocyanide tetraanion and two meriquinone dications. No measurement of solubility was made.

These four publications and that of Straus, supra, show that although the term, "salt", has been used to describe the blue precipitate formed when certain inorganic or unspecified salts were added in high or unspecified concentration to the blue product of oxidation of benzidine or several substituted benzidines, there has been no demonstration of the generality of the phenomenon, of the quantitative controllability of the phenomenon, of the solubilities of the products, or of the ionic nature of the product. The focus of this early work was on the structures of the blue dyes, but there was not even consensus on their chemical structure.

Although benzidine and substituted benzidines are most commonly used as chromogenic electron donors in oxidation by peroxide, at least some oxidase enzymes catalyze TMB oxidation by molecular oxygen (Miller and Nicholas (1984) *Analytical Biochemistry*, 140: 577-580). This fact is a reminder that improvements in the technology of visualizing oxidative reactions with benzidine or substituted benzidines have broad applicability beyond the field of peroxidase-based assays.

SUMMARY OF THE INVENTION

The present invention overcomes the above difficulties of applying benzidine or substituted benzidines to solid-phase and gel-phase assays in all oxidations which generate meriquinones from these compounds, including but not limited to peroxidative oxidations. It permits controllable precipitation of the meriquinone as solid salts of a wide range of anions, which salts under defined conditions are less soluble than the salts of acetate and phosphate ions commonly used in buffers for meriquinone peroxidative staining applications. Solubility is controlled by temperature, pH, anion concentration, total ionic strength, and choice of anion.

The invention also permits the formation of complexes between meriquinones and polymeric anions.

Crystalline salts as agents of detection may not adhere well to the surface of solid phases, so that the analytical signal is mechanically labile, and may disrupt important structures in histochemical and cytochemical analyses. Complexes between meriquinone cations and polymeric anions can solve this problem if the polymeric anion is adsorbed to, convalently attached to, or entrapped in a solid or gel phase. The formation of immobilized complex ions between meriquinone and polymorphic anions can reduce meriquinone solubility as effectively as does salt formation and create a more permanent localized color. Furthermore, such polymers cannot crystallize, and so should not disrupt microstructure in cytochemical and histochemical applications.

Also, precipitation of the salts and immobilization of the complexes permits localization of the meriquinone analytical signal on the surface of a solid phase or in a gel phase, thereby dramatically lowering the detection limits of solid- and gel-phase assays to provide increased quantitative sensitivity and qualitative discriminatory power over previously disclosed analyses. The value of this invention is most evident when TMB is used as a peroxidative electron donor. TMB is uniquely valuable as a chromogen because of its negligible carcinogenicity and high reaction rate, but hitherto has been of limited value in solid-phase and gel-phase assays because of difficulty in immobilizing the reaction product. As a result of this invention, TMB staining of peroxidative activity can be extended to Southern, Western, Northern, nucleic acid hybridization dot, and immunodot blots, and to immunohistochemical and immunocytochemical staining, analyses in which the added sensitivity of TMB (relative to the other chromogenic peroxidase substrates) is especially valuable for reducing detection limits. TMB staining of histochemical preparations may now be possible with greater permanence and fewer crystal-induced artifacts than previously were seen.

Finally, there is growing use in clinical diagnostics of "rapid" immunodiagnostic kits in which immune reactions are performed and detected in or above a filtration membrane and excess reagents are washed through the membrane to terminate reactions and to minimize analytical background. Trapping of the meriquinone as a crystalline salt or immobilized complex ion in or on the membrane is ideally suited to this application.

Specifically, the present invention relates to compositions of matter useful for visualizing biological materials which compositions comprise an immobilized or dissolved complex of a polymeric anion and the meriquinone of benzidine or a substituted benzidine. In another aspect, the present invention relates to compositions of matter useful for visualizing biological materials which compositions comprise a solid salt of the meriquinone of benzidine or a substituted benzidine, wherein the anion of the salt is the conjugate base of an unsaturated or an aromatic organic acid.

The complex ion is formed by binding of the meriquinone to any polymeric anion and has a color characteristic of the meriquinone, of the polymeric anion, and of the mole ratio of meriquinone to polymeric anion. Although often soluble in aqueous solvents, the complex ion can be made to form amorphous insoluble colored deposits either through adsorption to a wider range of solid or suspended materials or through attainment of approximate equivalence between meriquinone positive charges and polymeric anion negative charges. Specific examples of polymeric anions include dextran sulfate, polyphosphate, polyanethole sulfonate, polyacrylate, polymethacrylate, and a wide range of ion exchange adsorbents, but the composition of the complex ion is quite variable, allowing a wide range of degree of polymerization for the polymeric anion as well as a wide range of molar ratios of meriquinone to polymeric anion.

The solid salt is formed by reaction of charge-equivalent quantities of the meriquinone and a specific anion of limited size and charge, has a color characteristic of the meriquinone and of the anion, usually is crystalline, and usually will have a solubility below $10^{-3}$M when equilibrated with water in the absence of excess anion. The specific anions claimed as components of such salts include malate, tartarate, succinate, malonate, glutarate, oxalate, formate, pyrophosphate, isocitrate, ethylenedinitrilotetraacetate, 1,2,3,4-butane tetracarboxylate, fumarate, maleate, phthalate, isophthalate, terephthalate, benzoate, hemimellitate, trimellitate, trimesate, pyomellitate, mellitate, and mesaconate. The specific anions include all anions containing aromatic groups or unsaturated carbon chains. In addition, the anion may be sulfate, citrate, nitrate and halide (e.g., chloride, bromide, iodide, fluoride), if the substituted benzidine is TMB.

In another aspect, this invention relates to a solid phase or gel containing one of the compositions described above.

Preferably, the benzidine derivative is TMB. Also preferably the oxidized benzidine or its derivative is formed in the presence of a peroxide and a catalyst which is a peroxidase, a hemoprotein, or a protein-free iron porphyrin.

In a use aspect, the invention relates to analytical processes where a visual signal is generated (and sometimes later dissipated) by controlling the aqueous solubility of the meriquinone of benzidine or a substituted benzidine. Control is exerted primarily by addition of a quantity of polymeric anion or anion sufficient to achieve a meriquinone solubility below $10^{-5}$M, creating a precipitated or immobilized deposit with a characteristic color. A wider range of anions than specified above is effective for this task, each having a characteristic minimum effective concentration. As solubility is controlled by temperature, pH, anion concentration, total ionic strength, and the identity and concentration of any organic cosolvent, as well as by identity of the meriquinone and anion, there are many ways to achieve a desired solubility, including ways to dissolve the deposit (e.g., by lowering the concentration of precipitating anion or increasing the total ionic strength).

Preferably, the analytical process comprises oxidizing benzidine or a substituted benzidine to the meriquinone thereof at a pH of about 3 to 7, and in the presence of an effective (precipitating or immobilizing) concentration of an anion or polymeric anion, an oxidation catalyst, and an effective amount of oxidant, thereby forming a solid salt or immobilized complex of said anion or polymeric anion and said meriquinone having a controllable solubility as given above and characteristic color and solid form. The pH is preferably 3.5 to 4.5 if the oxidation catalyst is horseradish peroxidase and the benzidine derivative is TMB, and the TMB concentration is preferably near the solubility limit for the specified pH, i.e., is within a factor of two of the solubility limit of TMB.

Preferably, the oxidation catalyst is bound to a nucleic acid the sequence of which is complementary to a DNA sequence from the chromosome(s) of an organism or is bound to a non-catalytic protein such as an antibody, an antigen, avidin, a lectin, or Staphylococcal Protein A. Also preferably the visualization is achieved on a Southern blot, on a Northern blot, on a DNA or RNA dot blot, on a Western blot, on an antigen or antibody dot blot, in an immunodiagnostic or nucleic acid probes assay device, in a gel or on a paper or plastic strip (e.g., as used in electrophoresis, chromatography, or isoelectric focusing), on a nutrient gel plate containing cell colonies or on a mounted histological section or cytological smear.

In another embodiment, the invention relates to a process for visualizing a biological material contained in or on a test sample selected from the group consisting of a solid phase, a gel, a dissolved or suspended mixture containing complementary antibody and antigen, and a dissolved or suspended mixture containing complementary single-stranded nucleic acids, which process comprises forming the meriquinone solid salt or immobilized complex having a controllable solubility as given above and observing the resulting colored deposit.

In another embodiment, the invention relates to a process for detecting the presence of one or more antigens or antibodies in a liquid test sample, which process comprises:

(a) incubating the test sample or an extract thereof with a surface to capture the antigen or antibody and with a peroxidase-labeled antibody or antigen which binds to the antigen or antibody to be detected, these incubations occurring separately, in either order, or together;

(b) filtering the incubation mixture of step (a);

(c) washing the filter of step (b);

(d) incubating the washed product of step (c) with a benzidine or substituted benzidine and an effective concentration of an effective anion or polymeric anion to form a solid salt or immobilized complex with the meriquinone of said benzidine or substituted benzidine;

(e) filtering and washing the incubate of step (d); and (f) detecting the formation of said solid salt or immobilized complex of said anion or polymeric anion and the meriquinone of said benzidine or substituted benzidine, wherein said formation indicates the presence of said antibody or antigen.

The incubations of step (a) may take place together or separately in either order.

Preferably, the capturing surface is a filter membrane or beads suspended in the test sample above the filter membrane capable of capturing the analyte. Preferably steps (d) and (e) are carried out at a low ionic strength and a pH of 3.5–5.5. Alternatively, after step (f) the mixture is filtered and washed at a high ionic strength to remove the meriquinone, a peroxidase-labeled antibody or antigen different from that used previously in step (a) is incubated with the washed mixture to detect a different region of the antigen or antibody, or a different antigen or antibody in the test sample, the mixture is filtered, washed and incubated with benzidine or a substituted benzidine and an effective anion or polymeric anion, the resulting incubation mixture is filtered and washed, and the formation of the salt or complex is detected. Because of the control over meriquinone solubility introduced by this invention, such reprobing of an immunoassay test sample can be repeated many times.

Also within the scope of the invention are kits, generally in multicontainer format, for visualizing a nucleic acid, antigen or antibody in certain assay formats, which kits include instructions for how to precipitate or immobilize the meriquinone with an anion or polymeric anion and may supply the precipitant. The kits may also include the benzidine or substituted benzidine, and a detecting compound which specifically interacts with (binds to) the nucleic acid, antigen or antibody, which detecting compound is detected either directly through an attached peroxidase enzyme or indirectly through use of a compound which specifically interacts with the detecting compound and is conjugated to a peroxidase. An immunodiagnostic kit may also include a filter membrane, anionic latex beads, an anionic dipstick, or an incubation buffer containing an anion or polymeric anion which will precipitate the meriquinone of benzidine or substituted benzidine. If the solid support is anionic, the buffer need not contain a precipitant.

The meriquinones are generally more highly colored than the benzidines, which are commonly used reactants in peroxidative transformations catalyzed by peroxidase enzymes and by various heme proteins or protein-free hemes. Therefore, meriquinone formation in the presence of a peroxide indicates the simultaneous presence of a peroxidase or heme-containing compound, provided that non-enzymatic catalysis by certain transition-metal ions is prevented. Alternatively, meriquinone formation in the presence of a peroxidase, heme compound, or certain transition-metal ions indicates the simultaneous presence of a peroxide.

In applications where absence of peroxidase enzymes and hemes is assured, meriquinone formation in the presence of a benzidine and a peroxide can be used to detect the presence of certain transition metal ions with oxidation-reduction activity, chiefly the ions of iron, cobalt, nickel, maganese, chromium, copper, molybdenum, rhodium, ruthenium, platinum, and palladium. In addition, kits for detecting hemoglobin or heme are included within the scope of the invention. Analyses of peroxides and heme proteins (especially hemoglobin from blood) have obvious value in chemistry, biology, medicine, and forensic science. Peroxidases are less commonly the subject of direct study than tools in the highly sensitive analysis of any other compound for which a binding assay can be devised or the analysis of topological connectedness in compartmented systems, such as tissues, where injection of peroxidase into one part of a compartment is followed by its diffusion into all parts of the compartment but not into adjacent compartments.

BRIEF DESCRIPTION OF THE DRAWINGS

FIG. 3 represents a Western blot comparing TMB and diaminobenzidine (DAB) as substrates for visualizing HRP-labeled antibody against p21 ras protein.

DESCRIPTION OF THE PREFERRED EMBODIMENTS

Figure 1:
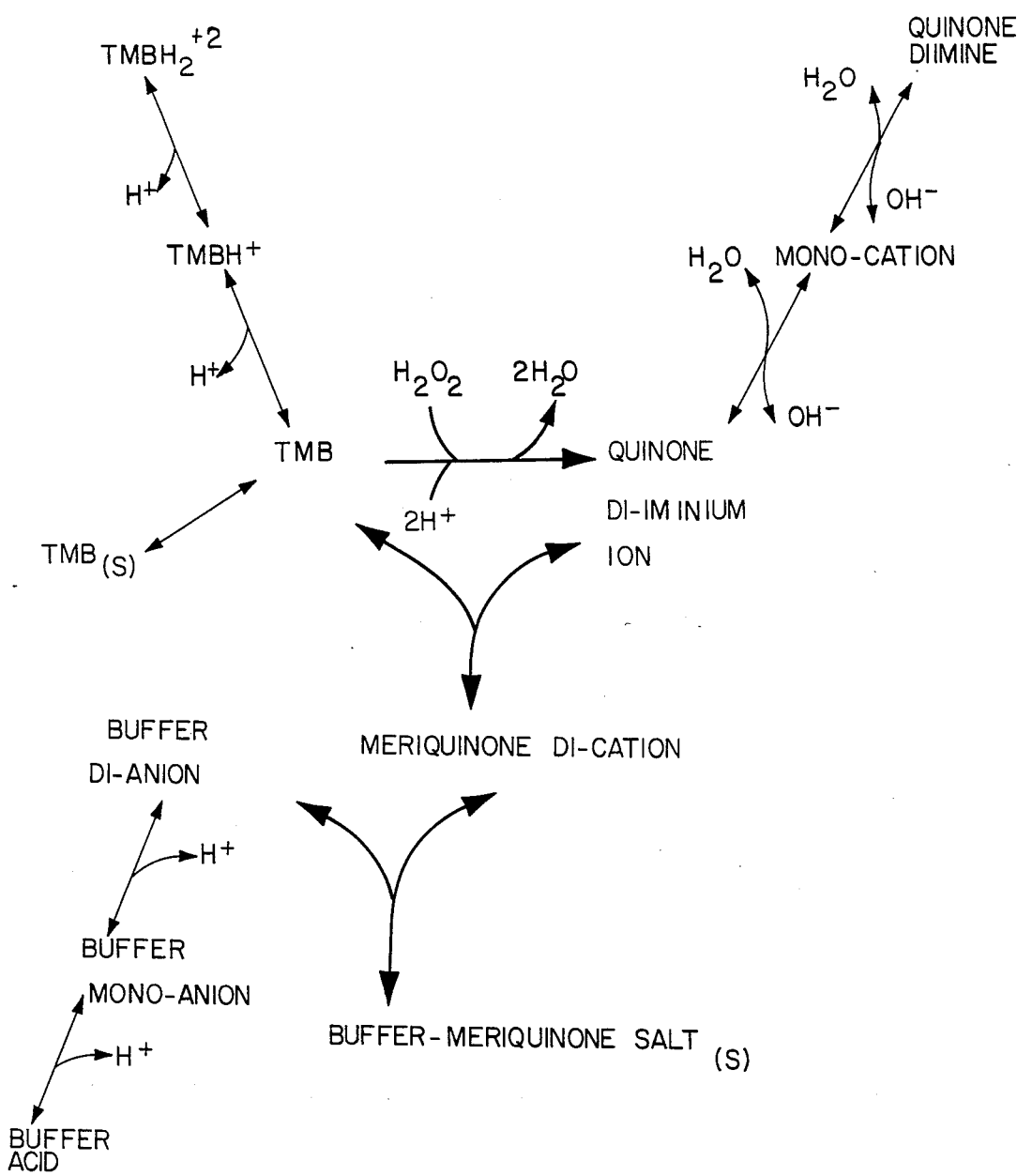
FIG. 1 depicts the coupled oxidation, charge-transfer complex formation, conjugation, and salt precipitation reactions which occur when benzidine or a substituted benzidine, such as TMB, is oxidized in the presence of a precipitating anion. It is drawn for a diprotic buffer acid, the di-anion of which forms an insoluble salt with the meriquinone. Similar networks can be drawn for buffer acids and precipitating anions with different stoichiometries.

Definitions:

As used herein, "substituted benzidine" refers to any compound of the general formula:

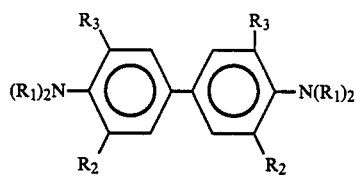

where $R_1$, $R_2$ and $R_3$ are independently taken from the following groups: H—, $CH_3$—, $NH_2$—, $CH_3O$—, $CH_3(CH_2)_n$—, $CH_3(CH_2)_n$—O—, CN—, $NO_2$—, F—, CL—, BR—, or I—, where n is an integer of from 1 to 10, preferably 1 or 2, and where $R_1$, $R_2$ and $R_3$ are not all H—. (In the parent compound, benzidine, $R_1$, $R_2$, and $R_3$ are all H—.) Representative derivatives include the following: 3,3',5,5'-tetramethylbenzidine, or TMB, ($R_1$ is H— and $R_2$ and $R_3$ are $CH_3$—), ortho-dianisidine ($R_1$ and $R_2$ are H— and $R_3$ is $CH_3O$—), ortho-tolidine ($R_1$ and $R_2$ are H— and $R_3$ is $CH_3$—), and diaminobenzidine ($R_1$ and $R_2$ are H— and $R_3$ is $NH_2$—). Preferably $R_1$, $R_2$ and $R_3$ are independently chosen from H—, $CH_3$—, $CH_3O$—, and $NH_2$—, and most preferably $R_1$ is H— and $R_2$ and $R_3$ are $CH_3$—.

As used herein, "quinone diimine" of benzidine or substituted benzidine refers to any compound of one of the general formulae:

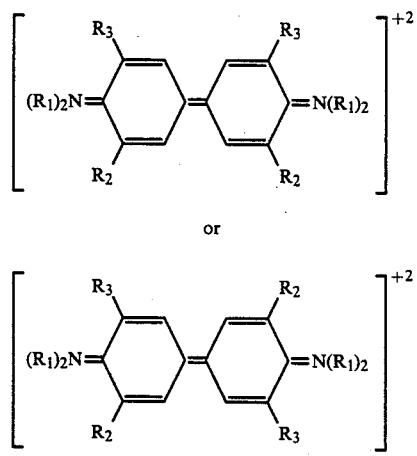

where $R_1$, $R_2$ and $R_3$ are specified above, and $R_1$, $R_2$ and $R_3$ can all be H— (if benzidine). If $R_1$ is H—, at pH values above the $pK_a$ values of one or both of the iminium groups, the molecule will have lost one or two protons from nitrogen atoms, having a net charge of +1 or 0, respectively.

As used herein, "meriquinone" of benzidine or substituted benzidine refers to a molecule having an oxidation state intermediate between that of the benzidine and its quinone diimine and consisting of a 1:1 noncovalent charge-transfer complex between the benzidine or substituted benzidine and its quinone diimine. Without adherence to any particular theory, it is believed, in view of the data found herein showing formation of crystalline salts of defined compositions with a wide range of anions, that in the pH region of 3-7 the meriquinone exists primarily as a dication. The equilibrium constant for formation of this complex normally is so favorable that most quinone diimine formed by oxidation of benzidine or a substituted benzidine will immediately form the meriquinone as long as unreacted parent compound is present.

As used herein, "peroxide" refers to any compound containing the peroxide (—O—O—) group, and preferably to any compound containing the hydroperoxide (—O—O—H) group. Examples of peroxides include, e.g., hydrogen peroxide, methyl peroxide, ethyl peroxide, isopropyl peroxide, tert-butyl peroxide, substituted cumene peroxides, urea hydrogen peroxide, and peroxy acids.

As used herein, "oxidation" refers to the abstraction of one or two electrons from benzidine or a substituted benzidine to form a meriquinone or quinone diimine. Preferably the oxidation herein uses a peroxide oxidant.

As used herein, "oxidation catalyst" refers to any compound which increases the rate of oxidation of benzidine or a substituted benzidine to the meriquinone or quinone diimine.

As used herein, "peroxidative catalyst" refers to an oxidation catalyst which catalyzes reduction of a peroxide to the related alcohol (or water if hydrogen peroxide is the oxidant) by a hydrogen donor such as an alcohol or amine. Subclasses of peroxidative catalysts include aquated or otherwise complexed transition metal ions which are reactive toward electron transfer (e.g., copper, iron, cobalt, maganese), hemes, hemoproteins, and specific enzymes known as peroxidases. A subclass of peroxidases, the "haloperoxidases", employ halide ion as a cofactor. The most commonly used peroxidase is purified from horseradish roots.

As used herein "solubility" refers to the concentration of a compound in solution when it is in equilibrium with a solid phase containing the same compound. If the compound is a cationic meriquinone (or any ion), the solid phase should contain a counter-ion of opposite charge in sufficient quantity to balance exactly the cationic charge, and the compound solubility will vary inversely with respect to counter-ion concentration in solution and (in most cases) directly with respect to temperature and ionic strength contributed by poorly precipitating electrolytes.

As used herein, "controllable" is used to describe properties of the meriquinone-containing solid phase such as the solubility, color, crystallinity, and crystal size, which can be selected simply by controlling the conditions under which the meriquinone is deposited in the solid phase. For example, solubility of the meriquinone salt is controlled by chemical identity of the anion, anion concentration, pH, temperature, and total ionic strength of the medium. Crystallinity and color are determined by the chemical identity of the anion. Crystal size may be controlled by the chemical identity of the anion, temperature, anion concentration, and the speed with which meriquinone is generated by oxidation of benzidine or a substituted benzidine.

As used herein, "biological material" refers to a substance or structure which is present in or extracted from a living or dead biological organism. Examples of biological materials include proteins, specific regions within proteins, nucleic acids, specific nucleic acid sequences, carbohydrates, subcellular structures, cells, and tissues.

As used herein, "visualizing" and "visualization" mean the detection of the biological material or identification or characterization of at least a portion or region of the biological material, the latter being exemplified by normal genetic polymorphism not associated with a disease.

As used herein, "test sample" refers to a solid phase such as a polymer, a gel, an histological section, or a cytological smear, or a liquid phase, including dissolved and suspended mixtures, such as is tested in an immunoassay or other diagnostic assay.

As used herein, "polymeric anion" refers to a polymer which has a negative ionic charge. Examples include polyacrylate, polymethacrylate, dextran, sulfate, sulfated glycosaminoglycans, polyglutamate, polyaspartate, carboxymethyl-cellulose, -dextran, or -agarose, sulfoethyl- or sulfopropyl-cellulose, -dextran, or -agarose, polyphosphate, polyanethole sulfonate, or any other suitable negatively charged polymer.

As used herein, an "effective amount of an effective anion or polymeric anion" refers to the amount of an appropriate anion or polymeric anion which will cause formation of a solid salt or immobilized complex of the anion or polymeric anion with the meriquinone of the benzidine or substituted benzidine, which ever is used in the process, which salt or immobilized complex has a meriquinone solubility below $10^{-5}$M.

As used herein, "tag" refers to a label moiety which contains or is capable of generating a radioactive, electron-opaque, colored or fluorescent material and is attached through strong binding to the probe protein or nucleic acid in question or to another molecule which binds to the probe in some fashion. An example is an enzyme such as a peroxidase which reacts with a substrate to form a detectable product and is coupled covalently to an antibody or to streptavidin.

As used herein, "detecting compound" refers to any compound which binds specifically to the biological material. For example, if the biological material is an antibody, the detecting compound may be an antigen containing an epitope which binds specifically to the antibody. If the biological material is a nucleic acid, the detecting compound may be a complementary strand of the nucleic acid capable of hybridizing thereto.

As used herein, "Western blot" refers to an analytical procedure in which (a) a mixture containing an antigen is separated by gel electrophoresis or isoelectric focusing, (b) the resolved components are transferred to an immobilized on a paper, glass fiber, or plastic sheet, and (c) the positions and identities of the components are determined by various methods which may create visible signals, including binding of a tagged antibody specific for the antigen in question or for another antibody which is specific for the antigen in question. This term also is construed to cover analyses in which (a) a mixture containing proteins bearing any sort of moiety recognized by a binding protein is subjected to electrophoresis or isoelectric focusing, (b) a blot of the separation pattern is prepared, and (c) the blot is visualized by exposure to the binding protein, directly or indirectly attached to a tag.

As used herein, "Southern blot" refers to an analytical procedure in which (a) a mixture containing various pieces of DNA is separated by gel electrophoresis, (b) the resolved DNA molecules are transferred to and immobilized in single-stranded form on a paper, glass fiber, or plastic sheet, and (c) the positions and identities of the components are determined by various methods which may create visible signals, including base-paired hybridization to a tagged polynucleotide probe of base sequence at least partially complementary to a targeted sequence of interest. The probe may be directly or indirectly tagged; in the latter case, the tag will be attached to another molecule which binds tightly to the probe.

As used herein, "Northern blot" refers to an analytical procedure in which (a) a mixture containing various pieces of RNA is separated by gel electrophoresis, (b) the resolved RNA molecules are transferred to and immobilized in single-stranded form on a paper, glass fiber, or plastic sheet, and (c) the position and identities of the components are determined by various methods which may create visible signals, including base-paired hybridization to a tagged polynucleotide probe of base sequence at least partially complementary to a targeted sequence of interest. The probe may be directly or indirectly tagged, as for Southern blots.

As used herein, "immunodot blot" refers to an analytical procedure in which an antigen in a mixture is immobilized on the surface of a paper, glass fiber, or plastic sheet and the presence of the antigen is determined by various methods which may create visible signals, including binding of a directly or indirectly tagged specific antibody. Alternatively, the mixture may contain an antibody which is identified with a directly or indirectly tagged antigen.

As used herein, "nucleic acid hybridization dot blot" refers to an analytical procedure in which a nucleic acid in a mixture is immobilized in single-stranded form on the surface of a paper, glass fiber, or plastic sheet and the presence of the nucleic acid is determined by various methods which may create visible signals, including base-paired hybridization to a directly or indirectly tagged polynucleotide probe of base sequence at least partially complementary to a targeted sequence of interest.

As used herein, "enzyme immunoassay" (EIA), also known as "enzyme-linked immunosorbent assay" (ELISA), refers to an analytical procedure in which an antigen or antibody in a mixture is detected via its binding to a complementary antibody or antigen immobilized in some fashion on any solid support or suspended particles, such that the binding generates a proportionate enzymatically generated signal, either attached to the support or liberated into a fluid medium which can be separated from the support or particles. There are many ways in which the signal can be linked to the binding event. In a "sandwich" method for antigens, the antigen is extracted from the mixture by a nonspecific adsorbent or bound to a specific "capture" antibody attached to the solid phase or suspended particles and specific probe antibody is bound to the immobilized antigen. The probe antibody may be conjugated to enzyme or may be detected by a molecule which binds to the probe antibody and is attached directly or indirectly to the enzyme. In the "sandwich" method for antibodies, the antibody is removed from the mixture by binding to antigen attached to the solid phase or suspended particles and in turn binds a probe molecule, such as another antibody or *Staphylococcus aureus* protein A, which binds to certain immunoglobulins. The probe may be conjugated to the enzyme or may be detected by a molecule which binds to the probe and is attached directly or indirectly to the enzyme.

As used herein, "immunohistochemical staining" refers to an analytical procedure in which a thin slice of a biological tissue (an "histological section") is attached to a glass slide and exposed to an antibody probe specific for an antigen which might be present in the tissue. The presence, location and approximate amount of antigen can be determined by microscopy after detection of the bound antibody via a directly coupled tag or exposure to another molecule which binds to the antibody and to which a tag has been coupled.

As used herein, "immunocytochemical staining" refers to an analytical procedure in which a suspension of cells (e.g. from blood or from cell culture) is spread across and attached to a glass slide (to form a "cytochemical smear") and exposed to an antibody or antigen probe specific for an antigen or antibody which might be carried by the cells. The presence, distribution, and approximate amount of antigen or antibody can be determined by microscopy after detection of the bound antibody or antigen via a directly coupled tag or exposure to another molecule which binds to the added antibody or antigen and to which a tag has been coupled.

Occasionally, histochemical or cytochemical staining for endogenous peroxidative or oxidative catalytic activity is performed by exposing histological sections or cytological smears directly to benzidine or a substituted benzidine, with or without added peroxide, but without mediation of an immunological reaction. In addition, enzyme-tagged nucleic acid hybridization is beginning to be used to identify specific genetic material in cells or subcellular fractions examined microscopically. All of these methods are included in the terms, "histochemical staining" and "cytochemical staining".

Modes for Carrying Out The Invention:

The invention herein is realized through the controlled formation of a solid salt of the meriquinone of a benzidine or a substituted benzidine having a solubility less than about $10^{-5}$M with respect to meriquinone. If a polymeric anion is present, the meriquinone may be contained in a dissolved or immobilized complex or a solid salt of the polymeric anion. The salt or complex is prepared by reacting the benzidine or substituted benzidine in aqueous solution at a pH of 3-7 with an oxidant in the presence of an oxidation catalyst and an anion chosen such that the salt or complex will have the desired solubility, color, crystallinity, or crystal size. The precipitated or immobilized salt or complex may be used to indicate the location of oxidative catalytic activity on a solid phase or in a gel, thereby allowing visualization of a biological material as defined above by color formation on the solid or in the gel. Alternatively, immobilization of the salt or complex may simply facilitate separation of the meriquinone from excess reactants.

The benzidine or substituted benzidine may be any of those defined above. Most preferably, the benzidine herein is TMB because it clearly lacks carcinogenic and mutagenic activity and is turned over by horseradish peroxidase, the preferred oxidation catalyst for most applications, with a very high catalytic rate and a very low rate of enzyme suicide. If the precipitates of the meriquinones of benzidines other than TMB are colored differently from that of TMB, however, double-specificity probing of solid-phase assays may be possible, where one probe is developed with TMB until the enzyme is inactivated, and another probe is then applied and developed with another benzidine substrate.

The structure of the solid salt of the meriquinone is believed to be represented by one of the following formulae, without limitation to any particular theory: $MA_2$, $MA$, $M_3A_2$ or $M_2A$ where A is the anion and M is the meriquinone.

Polymeric complex ions generally show no such stoichiometric limitations, other than that the positive charge donated by the meriquinone will not significantly exceed (and usually will be much less than) the negative charge from the polymeric anion.

The anion is usually part of the buffer but may be on the solid phase, as when (a) a membrane or other solid phase is treated with a polymeric anion which binds to it, prior to initiation of the oxidation reaction, or (b) the solid phase is a cation exchange polymer. The monomeric anion must be soluble in water and the polymeric anion can be water-soluble or insoluble. Generally, the monomeric anion can be any anion which can form a meriquinone salt with solubility less than $10^{-5}$M. Specific monomeric anions within this class include malate, pyrophosphate, maleate, fumarate, formate, oxalate, succinate, citrate, isocitrate, tartarate, phthalate, isophthalate, terephthalate, benzoate, hemimellitate, trimellitate, trimesate, pyromellitate, mellitate, mesaconate, ethylenedinitrilotetraacetate, 1,2,3,4-butane tetracarboxylate, malonate, glutarate and any other anions meeting the solubility definition. Sulfate, citrate, nitrate or a halide, may also be employed if TMB is the substituted benzidine. Preferably the anion is a di-anion or tetra-anion. Also preferred are anions which are conjugate bases of unsaturated or aromatic organic acids. An unsaturated organic acid is a carboxylate acid containing at least one carbon-carbon double bond and contains carbon, oxygen, and hydrogen atoms, optionally with nitrogen and/or sulfur atoms. An aromatic organic acid is a carboxylic acid containing at least carbon, hydrogen, and oxygen atoms and contains at least one aryl group.

It is noted that solubility of the meriquinone in the salt depends mainly on the anion structure (charge, size and shape), the anion concentration, and the total ionic strength of the medium. For example, in many instances monoanions such as acetate, formate and dihydrogen phosphate are much less effective precipitants of the salts than di-, tri- or tetra-anions such as oxalate, succinate, sulfate, citrate, pyrophosphate, and fumarate. Selection of an anion which is effective will depend on its ultimate use: the solubility desired, the color desired, and crystallinity. Preferred effective anions for lowest solubility value are maleate, sulfate (for TMB only), pyrophosphate, oxalate, succinate, glutarate, fumarate, benzoate, hemimellitate, trimellitate, trimesate, pyromellitate, mellitate, mesaconate, phthalate, isophthalate and terephthalate, and most preferred for effectiveness in precipitation are the planar anions such as oxalate, maleate, fumarate, phthalate, isophthalate, terephthalate, benzoate, hemimellitate, trimellitate, trimesate, pyromellitate, mellitate, and mesaconate.

The anion herein may also be an anionic detergent which is noncovalently bound to the solid support such as lauryl sulfate, taurocholate, or taurodeoxycholate. In addition the anion may be a polymeric anion as defined above. Preferred of such polymeric anions are polyacrylate, polymethacrylate, polyphosphate, polyanethole sulfonate, and dextran sulfate. A polymeric anion such as dextran sulfate may be combined with a monomeric anion such as fumarate.

In the event that the anion to which the meriquinone binds is not itself an effective chelator or transition metal ions and the intended oxidation catalyst is not an aquated or otherwise complexed (non-heme) transition metal, it is preferred to include in the reaction medium an effective amount of a suitable chelator, such as, for example, EDTA, o-phenanthroline, biphenyl, or the like, to block competing catalysis by trace transition metal ions (especially iron, copper, cobalt, nickel, and manganese) which might be present as impurities. Alternatively, but less conveniently, all or most components of the reaction system are exposed to an immobilized chelating agent, such as Chelex 100, a resin supplied by Bio-Rad Laboratories, either by batchwise mixing and filtration or decantation, or by passage through a bed of the immobilized chelating agent.

The invention herein in its most general form relies on the ability of benzidine are substituted benzidines to function as electron donors for oxidative reactions wherein the oxidant may be any electron acceptor, including, for example, oxygen or peroxide, in the presence of an oxidative catalyst. The benzidine or substituted benzidine may be used to locate the quantitate such oxidative activities by the appearance of a color when the benzidine is presented to the catalyst in the presence of oxygen or peroxide. Preferably, the electron acceptor is a peroxide. The peroxide may be supplied or may be generated by a separate oxidation reaction employing oxygen as oxidant and an oxidase enzyme as catalyst. In this case, precipitation or immobilization or meriquinone salts or complexes, which have easily visible color, will be employed to indicate the localized presence of peroxidative activity or to locate or quantitate peroxides, either as analytes or, in the case of hydrogen peroxide, as products of catalysts by certain oxidase enzymes. The peroxide for this purpose may be, but is not restricted to, hydrogen peroxide, any alkyl or aryl peroxide, such as, for example, methyl, etyl, t-butyl, and cumene peroxide, urea hydrogen peroxide, and the like. Preferably, the peroxide is hydrogen peroxide, a $C_1$–$C_{10}$ alkyl peroxide, cumene peroxide, or urea hydrogen peroxide, most preferably, hydrogen peroxide, methyl, ethyl or t-butyl peroxide, or urea hydrogen peroxide.

If peroxide is the oxidant, the oxidation catalyst specifically catalyzes the reaction of the benzidine or substituted benzidine with the peroxide. Preferably the catalyst is a peroxidase such as horseradish or turnip peroxidase, a hemoprotein, such as hemoglobin, or a protein-free iron porphyrin. Most preferably, the catalyst is horseradish peroxidase. The exact type of catalyst is chosen based on the ultimate use to which the meriquinone is put. For example, if the catalyst is a hemoprotein or iron porphyrin derived therefrom, the invention is preferably used to indicate the presence of blood in any body fluid such as urine, in fecal material, or in a forensic sample, or to indicate the occurrence of hemolysis in blood (via the presence of hemoglobin in cell-free plasma or serum). In such a use the heme or hemoprotein is generally free in solution and the peroxide and benzidine or substituted benzidine are adsorbed to or imbibed in a solid phase or gel, to which the solution is applied.

If the catalyst is a peroxidase enzyme, it is preferably used to detect an analyte. Examples of such assays include Western blots, Southern blots (where, for example, the membrane is treated with dextran sulfate which catches the blue meriquinone product on the membrane), Northern blots, nucleic acid hybridization blots, immunodot blots, immunohistochemical staining, immunocytochemical staining, EIAs (in solution or suspension), and the like. While the peroxidase (or other oxidation catalyst) may be supplied as by immobilization within or injection into organisms or cells at the site where color development is desired, it is preferably separately bound, directly or indirectly, to another molecule which specifically binds to the specific analyte to be detected. In a special application, oxidases and peroxidase enzymes are coupled to separate molecules which bind directly or indirectly to the analyte. This latter format reduces the background in the analyte binding assays because signal will appear only where the analyte is located in sufficient density to immobilize the catalysts in close proximity. Random non-specific binding of separate oxidase or peroxidase conjugates to the gel or solid surface will not generate hydrogen peroxide near a peroxidase molecule, and the peroxide will diffuse into the medium, away from the gel or solid support, before it has a chance to oxidize a benzidine or substituted benzidine to the colored meriquinone.

Examples of molecules which can be used to bind to the analyte include nucleic acids and non-catalytic proteins. The nucleic acids are preferably DNA or RNA comprising a nucleotide sequence which is complementary to a codon or anti-codon sequence from the chromosome(s) of an organism, preferably a living organism, such that hybridization will take place. Examples of organisms whose sequences are to be detected include viruses, rickettsials, bacteria and eukaryotes.

Examples of non-catalytic proteins which may be bound to the peroxidase include antibodies, antigens, hormone-binding proteins, avidin (including streptavidin), lectins, protease inhibitors, nucleic acid binding proteins, and antibody-binding proteins such as Staphylococcal protein A and anti-antibodies. For immunoassays, the non-catalytic protein is preferably an antibody which binds specifically to an organism or a component of an organism, preferably a virus, rickettsial, bacterium, protozoan, yeast, fungus, or cancer cell. For nucleic acid hybridization assays, the non-catalytic protein may be avidin or streptavidin, which will bind to a biotinylated hybridization probe.

If peroxide is used as the oxidant, it is most likely provided in solution along with the benzidine or substituted benzidine. However, separate application of these two reagents is also contemplated herein, where one or both reagents is present in solid form or incorporated into a gel. Likewise, the anion, including the polymeric anion, to which the meriquinone binds may be provided together with or apart from the peroxide and benzidine or substituted benzidine and may be provided dissolved in solution, suspended in solution, or incorporated into a gel or attached to a solid phase, either covalently or by adsorption. The polymeric anion may itself be the solid support with which the benzidine comes into contact. Any of these reagents may be applied to a solid phase in solution form and deposited by evaporation or addition of a precipitating solvent.

The crystallinity, crystal size, color, and solubility of the meriquinone salt or complex ion can be deliberately controlled by altering such non-exclusive factors as type of anion, anion concentration (the anion is usually the buffer employed), temperature, type of benzidine or substituted benzidine, the pH of the reaction medium, the ionic strength of the medium, and the type of solvent. FIG. 1 summarizes the coupled redox, precipitation and acid-base equilibria which control the outcome of the reaction, using TMB, peroxide, and a precipitating dianion. The figure shows how excess TMB will drive the two-electron reaction product into the meriquinone, and how the solubility of the salt depends critically on the pH. Too much acid will protonate the TMB and break up the charge-transfer complex or protonate the buffer anion and break up the salt. Too much base will deprotonate the quinone diiminium ion to break up the charge-transfer complex. The effective pH range herein is 3 to 7, preferably 3 to 6 for maximum salt precipitation. Increased anion concentration and lowered reaction temperature favor salt precipitation or complex ion formation, with anion concentrations of $10^{-3}$ to $10^{-1}$M and reaction temperatures of 0 to 60 C. being preferred. The optimal concentration of oxidant in the reaction medium for maximum insolubility will depend mainly on its type and the ultimate use of the salt, but for hydrogen peroxide will generally range from about $10^{-4}$ to $10^{-2}$M.

The reaction medium is necessarily aqueous to permit measurement of oxidative activity; however, the medium may contain an organic cosolvent to control the solubilities of both the benzidine or substituted benzidine reactant and the meriquinone product. Any organic cosolvent may be employed, in an amount not exceeding 30% by volume of the entire solvent, depending on the particular cosolvent utilized. Preferably the amount of cosolvent is from about 0 to 10%. Preferred cosolvents are those which solubilize the benzidine or substituted benzidine more than they do the meriquinone product and which are less inhibitory toward the oxidation catalyst than other solvents. Preferred cosolvents meeting these criteria using horseradish peroxidase as catalyst include isopropyl alcohol, ethyl alcohol and dimethyl sulfoxide.

The compositions of matter and processes of this invention may be used to visualize the presence of specific biological materials such as proteins, nucleic acids, and non-protein antigens. If the biological material is a nucleic acid, the process herein may occur, for example, in a Southern blot, Northern blot, or nucleic acid dot blot. The protein may be, for example, hemoprotein, an antibody or an antigen. If the protein is an antibody (monoclonal or polyclonal) or antigen, the process herein may occur, for example, in a Western blot, antigen dot blot, antibody dot blot, ELISA, immunohistochemical staining, immunocytochemical staining, or in cell culture, as by screening any population of bacteria, yeast or eukaryotic cultured cells for expression of an antigen which is native or genetically engineered. If the biological material is tissue, cells or subcellular structure, the process herein may occur, for example, in histochemical, cytochemical or cell ultrastructural staining, respectively.

The biological material may be localized (deposited in a small region) on a solid phase or contained in a gel or fluid. The solid phase may be the surface of a paper, membrane, or polymer fabricated in the form of, for example, a fiber, thread, sheet, bead, tube, dish, rod, or mesh. The solid phase of choice will be the one to which the meriquinone product adheres the best. The polymer may be, for example, cellulose, chemically modified cellulose, nylon, chemically modified nylon, fluocarbon, polyester, agarose, acrylic ester, acrylic amide, polystyrene, chemically modified polystyrene, and the like. The solid phase is preferably cellulose, nylon, nitrocellulose, polystyrene, or an ion-exchange polymer, in bead or sheet form. If a cation exchange polymer is used, the solid phase and the polymeric anion may be one and the same. Specifically included are uniform latex beads, particles, or microspheres, which usually have diameters below 10 $\mu$m and which often possess covalently attached anionic groups.

The gel may be, for example, polyacrylamide, agarose, starch, gelatin, or the like. Preferably the gel is polyacrylamide or agarose. The fluid may be any fluid from the body such as, e.g., blood, semen, mucus, pus, urine or saliva, or may be a chemical extract of a body fluid or of a culture medium.

In one aspect, the presence of the biological material in a solid phase, gel, or liquid can be detected, or a region (e.g., the HLA genes of human DNA) in the biological material can be characterized or identified, by:

(a) contacting the solid phase or gel with an oxidation catalyst bound to a detecting compound capable of interacting specifically with the biological material;

(b) incubating the solid phase or gel from step (a) under conditions whereby the detecting compound will interact with the biological material if it is present in the solid phase or gel;

(c) washing the solid phase or gel from step (b) to remove non-interacting detecting compound;

(d) adding to the washed solid phase or gel from step (c) benzidine or a substituted benzidine;

(e) subjecting the solid phase or gel to conditions under which the benzidine or substituted benzidine will oxidize to a meriquinone thereof if the oxidation catalyst is present (the conditions comprising a reaction temperature of 0 to 60 C., and an aqueous medium of pH 3 to 7 containing an effective amount of an oxidant) and wherein an effective amount of an effective precipitating or immobilizing anion is added during one or more of the above steps (a)–(e) (preferably (c), (d) or (e)); and (f) detecting the formation of a solid salt or immobilized complex of said anion or polymeric anion and said cationic meriquinone, wherein the effective meriquinone solubility is less than abut $10^{-5}$M, and wherein said formation indicates the presence or characteristics of the biological material.

In an EIA format, step (f) comprises adsorbing a visible quantity of the meriquinone to an anionic surface, adsorbing a visible quantity of an anionic complex of the meriquinone to a cationic surface, trapping a visible quantity of an insoluble salt of the meriquinone on a filter membrane, or trapping a visible quantity of the meriquinone adsorbed to microscopic anionic particles on a filter membrane.

Regarding step (e), three independent variables (apart from temperature) most strongly influence horseradish peroxide activity with TMB as chromogenic substrate: TMB concentration, $H_2O_2$ concentration, and pH. Net HRP activity, defined as total color yield in a specified reaction time interval, is a composite of two dependent variables, initial velocity and catalytic suicide rate constant, if the assay time interval is sufficiently short that substrates are not significantly depleted (likely near the detection limit of any enzymelinked assay). For relatively short assays (0–10 min.), however, suicide is not severe, and initial velocity is the most important indicator of enzyme activity. Initial velocity rises monotonically with TMB concentration, and is almost proportional to TMB concentration at a $H_2O_2$ concentration of greater than 2 mM. The pH dependence of initial velocity at constant TMB concentration indicates an optimum pH at 4. The pH dependence of TMB solubility indicates a monotonic and increasingly steep rise as the pH is lowered from 5. The pH dependence of initial velocity at saturating TMB indicates a four-fold increase from pH 5.0 to pH 4.0 and a much smaller increase in activity as the pH is decreased from 4.0 to 3.6. Therefore, a pH of 3.5–4.5 is the preferred pH range for step (e), more preferably pH 4.0, if the substituted benzidine is TMB and the oxidation catalyst is horseradish peroxidase. The optimum horseradish peroxidase assay conditions are at room temperature, pH 4.0, 0.4 mM (saturating) TMB, and 2–3 mM $H_2O_2$. The combined criteria of pH and saturating TMB have the most profound effect on net activity, a four-fold increase from pH 5.0, where the enzyme most commonly is assayed, to pH 4.0.

In another aspect, the presence of the biological material in a solid phase or gel can be detected by the same process except that the first two steps are replaced by the following three steps:

(a) contacting the solid phase or gel with a detecting compound capable of interacting specifically with the biological material;

(b) contacting the solid phase or gel from step (a) with an oxidation catalyst conjugated to a moiety capable of specifically interacting with the detecting compound; and (c) incubating the solid phase or gel from step (b) under conditions whereby the detecting compound will interact with the catalyst and with the biological material if it is present in the test sample.

After formation of the meriquinone salt or immobilized complex ion, the solid phase may be rinsed with an aqueous solvent, such as water, an aqueous buffer, or an aqueous solution of an organic solvent such as ethanol, to wash away excess peroxide and benzidine or substituted benzidine. The solid phase then may be air-dried or stored immersed in an aqueous solvent.

In preferred aspects of the above multi-step processes, the incubation time and temperature are 1–30 minutes at room temperature, the washing step to remove non-interacting detecting compound is carried out more than once at room temperature, and the treatment with benzidine or substituted benzidine is carried out for 1–70 minutes at room temperature in the presence of an organic cosolvent as described above which increases the solubility of the benzidine or substituted benzidine.

In one preferred embodiment the invention relates to processes for visualizing a biological material (which is an antigen, antibody or nucleic acid) contained in or on a solid phase using a Southern blot, Northern blot, DNA dot blot, RNA dot blot, Western blot, antigen dot blot or antibody dot blot. The steps of these processes mirror those described above generally except that (a) the test sample is specifically a solid phase, (b) the detecting compound is specifically an antibody against an antigen, an antigen or anti-antibody against an antibody or a nucleic acid hybridization probe containing a single-stranded nucleotide sequence which is complementary to a codon or anti-codon sequence which might be contained in a nucleic acid in the biological material, (c) the oxidant is specifically a peroxide, and (d) the oxidation catalyst is specifically a peroxidase.

In another specifically preferred embodiment, the invention relates to processes for visualizing an analyte in an enzyme immunoassay format, wherein the analyte may be an antibody or antigen which is suspended or dissolved in a fluid test sample.

In preferred embodiments of this process the substituted benzidine used is TMB, and the anion is added during the step where the solid phase is subjected to oxidation conditions. In other preferred embodiments, a polymeric anion is incubated with the test sample; and excess polymeric anion is removed by washing with an aqueous solvent prior to oxidation.

If the biological material is a nucleic acid, it is preferably DNA localized on a membrane in a Southern blot format, as described, for example, by U.S. Pat. No. 4,358,535. The detecting compound is preferably a DNA hybridization probe attained to biotin, and peroxidase is preferably horseradish peroxidase bound to an avidin, most preferably streptavidin. The precipitating or immobilizing anion or polymeric anion is preferably citrate, fumarate, polyphosphate, polyanethole sulfonate, polyacrylate, polymethacrylate and/or dextran sulfate.

The horseradish peroxidase-avidin or -strepavidin conjugate is preferably incubated with the probe-hybridized target DNA in a solvent containing a chaotropic agent or a detergent, or such solvent is used to wash the solid phase after the incubation. Use of such detergents or urea is found to reduce the enzymatic background of Southern blots caused by non-specific binding of enzyme conjugate to the solid support. This background reduction is necessary if the increased analytical sensitivity is to be translated into a reduced detection limit. Examples of suitable detergents for this purpose include one or more of the following: Triton X-100, Nonidet P-40, sodium dodecyl sulfate, Neodol 25-3S, Zwittergent 3-16, or taurodeoxycholate. Most preferably, the detergent is Triton X-100 or Nonidet P-40. Examples of chaotropic agents include urea and its monoalkyl or dialkyl homologues, preferably urea or 1,1-diethyl urea.

If the meriquinone salt is used to detect the presence of biological materials in nucleic acid hybridization assays, a polymerase chain reaction procedure may be employed to amplify the target sequence in the biological material using primers, DNA polymerase and nucleotides. The amplification preferably is instituted before addition of the detection system. Amplification is more fully described in copending U.S. Ser. No. 791,308 filed Oct. 25, 1985 to K. Mullis, and Saiki et al., *Science*, 230, 1530–1534 (1985), the disclosures of which are incorporated herein by reference.

Furthermore, the DNA hybridization probe herein is most preferably a circular M13 probe containing a "gapped circle". Such probe may be prepared by any technique, including the second-strand synthesis method described by Brown et al., (1982) *Gene*, 20: 139–144 or the in vitro hybridization of plus- and minus-strands described by Courage-Tebbe et al., *Biochim. Biophys. Acta*, (1982), 697: 1–5 and by Everett et al., *The EMBO Journal*, (1982) 1: 433–437, the entire disclosures of which are incorporated herein by reference. The gapped circle construct preferably is attached to biotin by means of a 4'-methylene-substituted-4,5',8-trimethylpsoralen moiety as described more fully in U.S. Pat. No. 4,582,789 issued Apr. 15, 1986, the disclosure of which is incorporated herein be reference. The most preferred of these biotinylated psoralen compounds is the compound of the structure:

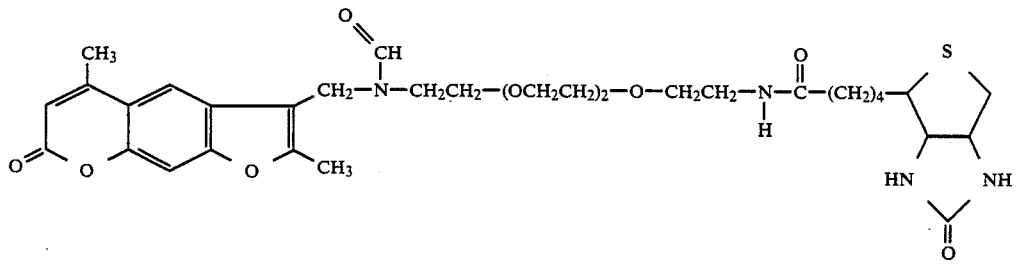

Also most preferably the probe is directed to an oncogene, the β-globin region of human DNA, or the human leulocyte antigen (HLA) region of human DNA. HLA probes are described more fully in the above-referenced K. Mullis et al. application and in U.S. Pat. No. 4,582,788 issued Apr. 15, 1986 to H. Erlich, the disclosure of which is incorporated herein by reference.

In another preferred embodiment herein, the biological material is an antigen or antibody to be detected in a Western blot format, with the detecting compound necessarily being an antibody specific for (which binds to) the antigen to be detected or an anti-antibody or antigen specific for the antibody to be detected. The peroxidase is preferably horseradish peroxidase conjugated to an antigen, anti-antibody or antibody capable of specifically interacting with the detecting compound, and the precipitating anion is dextran sulfate and/or fumarate. More preferably, the biological material is a ras p21 protein antigen, the detecting compound is an antibody directed to a specific mutant of the protein, and the horseradish peroxidase is conjugated to an anti-antibody specific for the detecting compound. The antibodies specific for a mutant of the normal p21 ras protein and their generation are described more fully in copending U.S. patent application Ser. No. 661,909 filed Oct. 17, 1984 to F. McCormick et al., the disclosure of which is incorporated herein by reference. Essentially peptides mimicking the region surrounding the amino acid at position 12 of the p21 protein (normally serine) are generated and injected into rabbits, yielding mutant-specific polyclonal antibodies. The anti-antibody may be, for example, a goat anti-rabbit IgG conjugated to horseradish peroxidase and directed against the mutant-specific antibodies. For Western blots preferred anions are a combination of fumarate and dextran sulfate, or pyrophosphate alone. The results are found to be much more sensitive and durable when dextran sulfate is used with fumarate rather than if fumarate is used alone as anion.

The major advantage of the present invention over what is described in the literature is that it permits TMB to be used in a wide range of analyses of peroxidative activity in which the reaction product must be deposited from solution at the site of generation or must be separated from unreacted reagents (e.g., to minimize background). The peroxidase substrates previously known to form insoluble products do so with lower catalytic activity, giving lower analytical sensitivities. In addition, the precipitation or complexation of the meriquinone concentrates color into a relatively small volume and prevents its diffusion throughout the analytical system. Such localization increases analytical sensitivity, as absorbance is proportional to chromophore concentration, which is inversely proportional to the volume through which the chromophore is distributed. Concentration of the analytical signal permits visual evaluation of the presence of the analyte without resorting to expensive or sophisticated instrumentation and facilitates storage or optical recording of a permanent record. It also permits washing to remove unreacted reagents which might otherwise increase the analytical background. Finally, some assays require knowledge of the location of the analyte as a specific site (via localization of the visible signal which its presence generates) to identify or characterize the analyte and distinguish it from alternatives.

The invention herein provides other potential improvements over known procedures. As the meriquinone salts of certain anions have different colors from those of other anions, choice of anion provides some latitude in choice of optimum color for a given application. The color of the salt or complex ion formed ranges from black to green. As the meriquinone salts have solubilities ranging over many orders of magnitude, choice of salt might be used to enhance contrast in the spatial distribution of color in a gel or on the surface of a solid. Salt solubility can be manipulated so that areas containing high concentrations of analyte supply sufficient meriquinone to precipitate with a given anion, whereas those with lower levels of peroxidative activity supply too little meriquinone to precipitate before it diffuses from the gel or surface. Such contrast enhancement can be used to improve the distinction between analytical "signal" and "background." Finally, polymeric anions form amorphous rather than crystalline deposits with meriquinone, thereby avoiding artifacts observed in histochemical or cytochemical analyses when crystal grow too large. In addition, amorphous deposits generally adhere more strongly to surfaces than crystals do.

Specific applications herein for the use of the immobilized or precipitated meriquinone in visualization include any context in which an oxidative activity is measured and localized in space, i.e., where the reaction product does not move from the site of generation. Examples include but are not limited to: (1) Southern blots visualized by horseradish peroxidase (HRP)-streptavidin (SA) conjugates bound to biotinylated DNA probes hybridized to specific genomic or cDNA sequences; (2) Northern blots detected in a similar manner after hybridization to specific RNA sequences; (3) DNA or RNA dot blots (e.g., for infectious diseases) detected in a similar manner; (4) Western blots visualized by HRP-streptavidin conjugates bound to biotinylated first or second antibodies or by HRP-derivatized first or second antibodies; (5) antigen dot blots visualized in a similar manner; (6) antibody dot blots detected with HRP-streptavidin conjugates bound to biotinylated antigen or with HRP-derivatized antigen; (7) any sort of binding assay in which one reagent is localized on a solid phase or in a gel and the other reagent is linked directly or indirectly to a peroxidase; (8) tests for blood in feces or urine or for hemolysis in plasma; (9) forensic chemical tests for blood; (10) histochemical or cytochemical staining of peroxidase-containing, peroxidase-labeled, or immunoperoxidase-labeled cells; and (11) screening of microbial colonies for expression of an antigen, native or introduced by genetic engineering.

In a different but overlapping set of applications, immobilization of the reaction product permits filtration or decantation followed by washing to remove unreacted reactants, thereby terminatng reaction in a controlled manner, reducing background, and simplifying creation of a permanent record. In addition to those listed above, these applications include enzyme immunoassays.

Kits of components which can be used to detect antibodies, antigens, or nucleic acids in solution, in suspension, on histochemical sections, on cytochemical smears, or in or on solid or gel phases, as in Southern blots, Northern blots, DNA or RNA dot blots, Western blots, antigen dot blots, antibody dot blots, and solution-phase enzyme immunoassays are also within the scope of this invention. The essential feature of such a kit is that it contains instructions which result in the immobilization or precipitation of the meriquinone of benzidine or a substituted benzidine by application of a polymeric anion or an effective concentration of an effective anion to give the meriquinone a solubility of less than $10^{-5}$M. Optional components include (a) benzidine or a substituted benzidine; (b) materials for preparing solutions (e.g., incubation buffers) containing the precipitating anion or polymeric anion, or the solutions themselves; (c) a peroxide in dissolved or pure form; (d) a peroxidative or oxidative catalyst, probably coupled to another compound which binds directly to the analyte or which reacts with a compound which binds to the analyte; (e) a non-anionic filter membrane or a solid phase which can adsorb the analyte in a specific or nonspecific manner, such as an anionic trapping component including, for example, a filter membrane, latex beads, a dipstick or a cation-exchange resin (where "anionic" means a surface bearing fixed negative charges); and (f) one or more control samples, such as tagged (e.g., biotinylated) molecular weight markers, chromosomal DNA or ribosomal RNA for kits detecting nucelic acids, nonspecific and specific immunoglobulins for kits detecting antigens (e.g., non-specific (not limited to mutants) polyclonal and monoclonal antibodies against p21 protein), and antigen-containing samples for kits detecting antigens. Other components of the kits such as wash buffers and stabilizers are also within the scope of this invention, as are kits which contain test strips imbibed with and dried with the benzidine or substituted benzidine, the precipitating anion or polymeric anion, and a peroxide.

Also within the scope of this invention are kits for detecting oxidative catalysts such as peroxidases, oxidases, hemoproteins, hemes, and transition metal ions, provided that they instruct the user to precipitate or immobilize the meriquinone of benzidine or a substituted benzidine by applying a polymeric anion or an effective concentration of an effective anion. The kit may detect all or part of a gene from an HTLV III virus, an HLA gene, all or part of the gene for a normal or mutant hemoglobin, or all or part of a normal or mutant oncogene. The antigen may be human chorionic gonadotrophin, human lutinizing hormone, and pathogenic organisms such as *Neisseria gonorrhea*, *Chlamydia*, or *Herpes simplex* virus.

The embodiments of the invention will be illustrated further by the examples which follow. In the examples all parts and percentages are by weight if solids and by volume if liquids, unless otherwise indicated. Temperatures are in degrees Celsius.

EXAMPLE 1

Formation and Description of Solid Salts of the Meriquinone of 3,3',5,5'-Tetramethylbenzidine (TMB)

Fifty ml volumes were prepared of 0.2 mg/ml TMB (Miles Laboratories), 0.0015% $H_2O_2$, 10% ethanol in each of the following pH 5.0 buffers: 0.10M sodium acetate; 0.10M sodium formate; 0.10M sodium phosphate, 0.10M sodium sulfate, 0.010M sodium acetate; 0.10M sodium pyrophosphate, 0.010M sodium acetate; 0.10M sodium fumarate; 0.10M sodium maleate; 0.10M potassium oxalate; 0.10M sodium malonate; 0.10M sodium succinate; 0.10M sodium glutarate; 0.10M sodium citrate; 0.10M sodium malate; 0.10M sodium tartarate; 0.10M sodium isocitrate; 0.10M potassium phthalate; 0.10M potassium ethylenedinitrilotetraacetate (EDTA); 0.10M sodium 1,2,3,4-butane tetracarboxylate; 0.025M potassium isophthalate, 0.025M potassium terephthalate (final pH=5.4, not 5.0); 0.07% sodium polyacrylate (MW 2000); 0.70% sodium polyacrylate; 0.10% sodium dextran sulfate (MW 500,000); and 1.0% sodium dextran sulfate. To each was added approximately 1 μg of horseradish peroxidase at room temperature. Each sample turned dark blue to black within a few seconds after addition of the enzyme. After 15-30 minutes, the reaction mixtures were started chilling to approximately 5 C. After standing overnight, they were spun in a Beckman J2-21 centrifuge (JA-17, head) at $10^4$ rpm, 0 C. for 135 min. The light but copious precipitates were incompletely pelleted by this procedure. After removal of most of the clear supernatants, the remaining suspended crystals were pelleted by 5 min spins at 5 C. in 1.5 ml polypropylene Eppendorf tubes in a Fisher micro-centrifuge.

All of the reaction mixtures except acetate and dextran sulfate yielded final pellets occupying 0.1-0.3 ml. There were a few crystals in the chilled acetate buffer, not enough to recover for physical study. Neither dextran sulfate preparation yielded any crystals, although the violet-black hue of the solution suggested that some reaction of the meriquinone with dextran sulfate (presumably to form a complex ion) had occurred, as the dissolved meriquinone is blue, not violet. Examination with a microscope with polarizing optics of all of the precipitates except that with polyacrylate showed a birefringent crystal form consisting of short or long needles. The polyacrylate precipitates were non-birefringent amorphous solids. The precipitate of 1,2,3,4-butane tetracarboxylate was a mixture of birefringent crystals and non-birefringent amorphous particles. The various precipitates had characteristic colors which depended on the anions used to prepare them, as shown in Table I.

TABLE I

| Colors of Salts and Complex Ions of the Meriquinone of TMB (second color in hyphenated expression is dominant) | | |
|---|---|---|
| Principal | Color | |
| Anion | Bulk Solid* | Crystal † |
| Acetate | blue | — |
| Phosphate | blue-black | grey-blue |

TABLE I-continued

Colors of Salts and Complex Ions of the Meriquinone of TMB
(second color in hyphenated expression is dominant)

| Principal Anion | Color Bulk Solid* | Crystal † |
|---|---|---|
| Malate | blue-black | grey-green |
| Pyrophosphate | violet-black | violet-blue |
| Dextran sulfate | violet-black! | violet ‡ |
| Sulfate | violet-black | black |
| 0.07% Polyacrylate | black | green-black |
| 0.7% Polyacrylate | green-blue | green-blue |
| Maleate | blue-violet | gray-green |
| Fumarate | royal blue | blue-green |
| Formate | royal blue | green-blue |
| Oxalate | royal blue | blue-green |
| Succinate | royal blue | blue-green |
| Citrate | royal blue | blue-green |
| Isocitrate | royal blue | green-blue |
| Tartarate | royal blue | blue-green |
| Phthalate | royal blue | blue-green |
| Isophthalate | royal blue | blue |
| Terephthalate | royal blue | blue-green |
| EDTA | royal blue | green-blue |
| 1,2,3,4-butane tetracarboxylate | royal blue | green-blue |

*reflected ambient fluorescent illumination
† = transmitted tungsten-halogen illumination at 20× magnification
! = reflected from concentrated solution (no solid)
‡ = transmitted through solution (no solid)

Most of the bulk solids showed a rich violet-blue hue which we have called "royal blue". Under transmitted illumination, their crystals showed a combined green and blue color. However, a significant subset of the solids were much darker—black or almost black. They showed a range of violet, blue, and green hues with transmitted light. The color contrast between the amorphous solids precipitated from two different concentrations of polyacrylate may provide some hint as to why some salts and complexes are darker than others. Meriquinone molecules complexed to 0.07% polyacrylate must be much closer to one another on the polymer chain than those complexed to 0.7% polyacrylate. Increased proximity dramatically darkens the color.

The amorphous nature of the polyacrylate-meriquinone precipitates suggests that polymeric anions should be especially useful precipitants in histochemical and cytochemical analyses, where crystals might destroy the ultrastructure which is a major focus of study.

EXAMPLE 2

Solubilities of Salts of the Meriquinone of TMB

I. Determination of Stoichiometry from the Anion Concentration Dependence of Meriquinone Solubility If a dissolved meriquinone, $M^{+m}$, is in equilibrium with the solid salt which it forms with an anion, $A^{-a}$, thermodynamic law requires that the following equilibrium expression be obeyed:

$$[M^{+m}][A^{-a}]^{m/a} = K_{eq}.$$

This equation has the following logarithmic form:

$$\log ][M^{+m}] + m/a \log [A^{-a}] = \log K_{eq}.$$

$[M^{+m}]$ is simply the solubility of the meriquinone. This equation predicts that a plot of log solubility versus log of the anion concentration should be a straight line with a slope of $-m/a$. This slope gives the stoichiometric ratio of anion to meriquinone in the salt. Many of the buffer anions used in this study can be expected to have different values of the anionic charge, a, in different pH regions, because they are conjugate bases to diprotic, triprotic, or tetraprotic weak acids. However, some, like sulfate and formate, can have only one value for a at accessible pH values. If m/a is measured for them, m can be calculated. Presumably the meriquinone retains this net charge in all salts which it makes in the relevant pH range (4–7). Therefore once m is evaluated for one salt and m/a is evaluated for other salts, the quotients of these values gives a values for the other salts.

The experiment described here used the preceding theory to estimate m and a for seven salts. Preliminary solubility studies suggested that the equilibrium concentration of $[M^{+m}]$ for each of these salts could be accurately measured at room temperature if $[A^{-a}]$ ranged from $10^{-3}$ to $10^{-2}$M. To keep the ionic strength approximately constant during the study of the buffer anion concentration dependence, $10^{-1}$M Na acetate was included in all of these buffers, along with 10% ethanol to increase the solubilities of both TMB and the meriquinone. Preliminary studies had shown that the acetate salt of the TMB meriquinone is so soluble that any precipitate seen would contain the other buffer anion in the mixture, not acetate.

A series of buffers were constructed, all pH 5.0 at room temperature, 10% in ethanol, and 0.10M in sodium acetate, and either $10^{-3}$M, $3 \times 10^{-3}$M or $9 \times 10^{-3}$M in one of the following electrolytes: sulfate, pyrophosphate, oxalate, succinate, maleate, fumarate, or citrate. These are stoichiometric concentrations, uncorrected for ionization at pH 5.0. The corresponding solid meriquinone salts obtained in Example 1 were washed three times in $10^{-2}$M concentrations of the correspnding pH 5.0 buffers (containing no ethanol), by vigorous mixing to resuspended the pellet followed by spinning for several minutes in a Fisher micro-centrifuge. Each wash involved a total volume of 1.5 ml (pellet volume of about 0.3 ml) in an Eppendorf polypropylene centrifuge tube. Then 20–50 μl of washed, pelleted meriquinone salt and a few mg of TMB were mixed in 2 ml of the buffer containing the same anion, in a glass tube, covered, and shaken in a Blue M Magni Whirl thermostated water bath at 25.2±0.1 C. At 30–60 min intervals, the crystal suspensions were spun 3–5 min at room temperature in a Fisher micro-centrifuge. The supernatant solutions were withdrawn carefully from the light and delicate pellets with Pasteur pipettes and scanned in a Hewlett-Packard 8450A spectrophotometer between 260 and 700 nm. After scanning, the solutions and pellets were returned to the equilibration tubes for renewed shaking. Repeat measurements were taken until precision within 20% was obtained. Often only two and no more than three measurements were needed on each sample to reach this degree of reproducibility, indicative of complete equilibration of solid and solution phases; most repeat measurements agreed to within 5%. Care was taken to assure that solid meriquinone salt and solid TMB were present in each tube. Excess (saturating) TMB was added to suppress the dissociation of meriquinone charge-transfer complex into component quinone diimine and TMB (see FIG. 1). This precaution does not change meriquinone solubility, but simplifies its measurement. These spectra contained absorbance peaks at 370 and 650 nm characteristic of meriquinone and a very small shoulder at 450 nm assigned to quinone diimine; a much larger peak near 280 nm confirmed the presence of excess TMB. All spectra had the same shape, regardless of the precipitating anion or the color of the precipitate. Meriquinone concentration was calculated from $A_{650}$ assuming a molar extinction coefficient of $3.9 \times 10^4 M^{-1} cm^{-1}$ (Josephy et al., (1982) *Journal of Biological Chemistry*, 257: 3669–3675). If the concentration was too high to measure undiluted with a 1 cm light path, the scan was performed on an undiluted sample with a 2 mm light path or an appropriately diluted sample (later discarded) with a 1 cm light path.

Once solubility equlibria were established at 25.2 C., all of the tubes were transferred to an ice-water bath. Solubilities at 0 C. were determined for all solutions in which they were high enough for accurate measurement.

Figure 2:
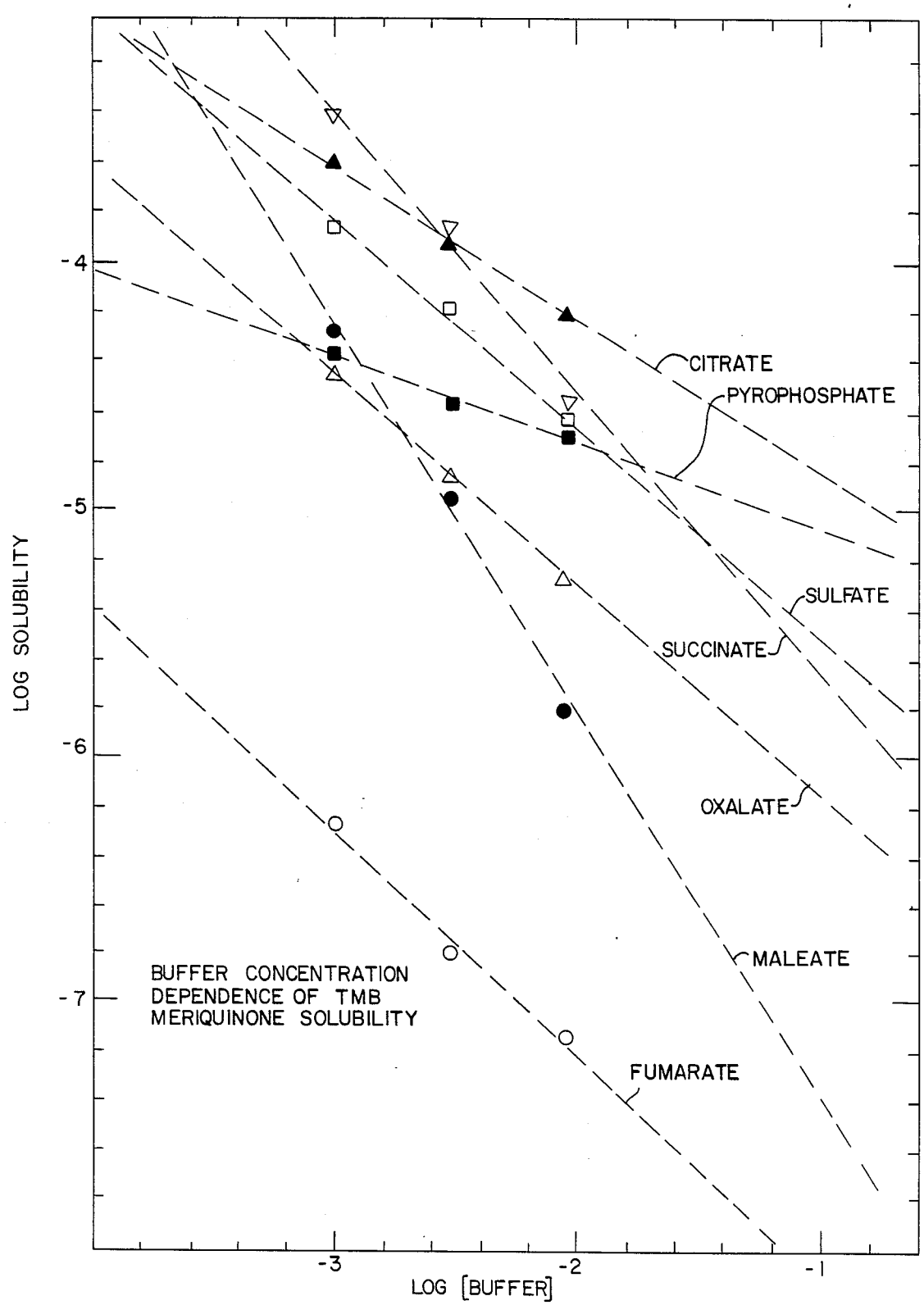
FIG. 2 graphs log meriquinone solubility against log anion concentration for seven precipitating anions and the meriquinone of TMB. The stoichiometries of the meriquinone salts can be deduced from the slopes of these plots. In the figure, A is fumarate, B is maleate, C is oxalate, D is succinate, E is sulfate, F is pyrophosphate, and G is citrate.

FIG. 2 contains the log solubility versus log anion concentration graphs from which the salt stoichiometries were estimated. These plots also dramatically illustrate the range of solubility, over more than 3 orders of magnitude for different salts. The dashed lines were visually fitted. Table II summarizes the stoichiometry estimates, based on rounding the slope to the nearest integral or fractional value giving integral values for m and a. For example, the sulfate slope of 0.9 is close enough to 1.0 to suggest a 1:1 ratio of M to A in this salt; the same approximation was made for fumarate, oxalate, and succinate salts. As sultate must be a di-anion at any close to 5, the meriquinone must be di-cation. It should be a di-cation in all of the salts. Therefore, the citrate slope of 0.62 is so close to an m/a value of ⅔ that citrate must precipitate as a trianion. The pyrophosphate slope of 0.4 is close enough to an m/a value of ½ that pyrophosphate must precipitate as a tetra-anion. The maleate slope suggest crystallization as a monoanion, although a di-anionic structure might have been predicted.

TABLE II
Stoichiometries and Solubilities of Some Salts of the Meriquinone of TMB

| Anion | Slope | m/a* | m | a | Molar Solubility in 0.1 M Anion† |
|---|---|---|---|---|---|
| Sulfate | 0.9 | 1.0 | 2 | 2 | $3 \times 10^{-6}$ |
| Succinate | 1.1 | 1.0 | 2 | 2 | $2 \times 10^{-6}$ |
| Oxalate | 0.8 | 1.0 | 2 | 2 | $7 \times 10^{-7}$ |
| Fumarate | 0.9 | 1.0 | 2 | 2 | $7 \times 10^{-9}$ |
| Maleate | 1.6 | 2.0 | 2 | 1 | $4 \times 10^{-8}$ |
| Citrate | 0.62 | 0.67 | 2 | 3 | $1 \times 10^{-5}$ |
| Pyrophosphate | 0.4 | 0.5 | 2 | 4 | $9 \times 10^{-6}$ |

*nearest rational value for slope
† = extrapolated

Table III summarizes the temperature dependences of solubility for the seven salts, averaged for the different stated concentrations of each salt. The buffers were all adjusted to pH 5.0 at room temperature, but would have somewhat different pH values at 0 C (usually lower by 0.2–0.3 pH units). Such strong temperature dependences indicate high values for heats of solution, characteristic of ionic lattices.

II. Comparison of the Solubility Properties of TMB and Its Meriquinone

When the same methodology was applied to measure the solubility of TMB in a series of buffers (each pH 5.0 and 0.10M in a single anion) the data in Table IV were collected.

TABLE III
Temperature Dependence of Solubility for Some TMB Meriquinone Salts

| Anion | Solubility Ratio: 25.2 C/0.0 C |
|---|---|
| Sulfate | 6.9 |
| Succinate | —* |
| Oxalate | 8.4 |
| Fumarate | 5.6 |
| Maleate | 8.1 |
| Citrate | 9.6 |
| Pyrophosphate | 3.7 |

*the succinate salt solubility ratio ranged from 39 to 3 as the anion concentration was raised from $10^{-3}$ to $10^{-2}$ M, suggesting a change in crystal form at low temperature

TABLE IV
Solubility and Its Temperature Dependence for TMB in Several Buffers

| Anion | Solubility at 30.9 C (mM) | Solubility Ratio: 30.9 C/0.0 C |
|---|---|---|
| Sulfate | 0.15 | 1.9 |
| Oxalate | 0.16 | 12 |
| Fumarate | 0.16 | 3.9 |
| Maleate | 0.21 | 7.6 |
| Citrate | 0.17 | 2.3 |
| Phosphate | 0.16 | 2.0 |
| Acetate | 0.17 | 2.4 |
| Malonate | 0.16 | 1.8 |
| Glutarate | 0.17 | 2.0 |

For most buffer ions, the behavior of TMB stood in stark contrast to that of its meriquione. Solubility was independent of buffer ion, and the temperature dependence of solubility was low and independent of buffer ion. This behavior is expected of a molecular, as opposed to an ionic, crystal lattice. At pH 5.0 TMB must have a molecular charge close enough to 0 that it tends to crystallize in an un-ionized state. Oxalate and maleate and possibly fumarate violated this simple picture for TMB, at least at 0 C. At temperatures in the 25–30 C. range, TMB in these buffers had the same solubility as TMB in the other buffers, suggesting crystallization in a molecular lattice. However, at 0 C., TMB was significantly less soluble in these buffers than in the others; this phenomenon suggest that ionic lattices, with higher heats of solution, are preferred at low temperature for these two or three buffers.

The TMB and meriquinone salt solubility data present several important practical consequences for the analytical use of TMB oxidation.

(1) Some buffers, such as fumarate, maleate, and oxalate, should be more effective in localizing and immobilizing meriquinone as insoluble precipitates at the site of generation than other buffers, such as citrate and pyrophosphate. (Other buffers, not described in the preceding solubility studies, such as acetate, formate, and phosphate, are even less effective in precipitating meriquinone).

(2) Meriquinone salt solubility can be effectively controlled by varying the buffer concentration. The sharpness of control depends on the charge on the anion in the crystal lattice. If it is desired to reduce the solubility of a given salt, simply increase the buffer concentration.

(3) Meriquinone salt solubility can be effectively controlled with temperature. Low temperatures dramatically reduce solubility.

(4) The difference in solubility behavior between TMB and its meriquinone means that steps taken to reduce the solubility of the product will have no or only a modest effect on the solubility of the reactant (for which a high value normally is desirable). This fact simplifies the optimization of analytical procedures.

(5) The ionic strength dependence of solubility may provide a simple test of whether the colored deposit formed by oxidation of benzidine or a substituted benzidine contains the meriquinone or represents the non-ionic polymer which can form upon further reaction of the quinone diimine.

EXAMPLE 3

Immobilization of the Meriquinone of TMB by Polymeric Anions Bound to Solid Phase Adsorbents I. Cationic Adsorbents Polyacrylic acid (mean MW 2000, Aldrich Chemical Co. catalogue number 19,202-3) was dissolved in water to a concentration of 0.7% and adjusted with NaOH to pH 4.4. Dextran sulfate (sodium salt, mean MW 500,000, Pharmacia Fine Chemicals catalogue number 17-0340-02) was dissolved in water to a concentration of 1.0% and adjusted with HCl to pH 4.8. Separate $11 \times 1$ cm strips of three cationic adsorbents manufactured in sheet form (Zeta-Probe charge-modified nylon, Bio-Rad Laboratories; DE81 DEAE-cellulose paper, Whatman; ET81 Ecteola-cellulose paper, Whatman) were incubated two hours at room temperature in approximately 20 ml volumes of the 0.7% polyacrylate, the 1.0% dextran sulfate, or water, and washed once in similar volumes of water. The strips were then used to line the vertical walls of the wells in Falcon 3046 6-well microtiter dishes. The wells were filled with 8 ml volumes of 0.20 mg/ml TMB, 0.00075% $H_2O_2$, 10% ethanol in either 0.10M Na citrate or 0.10M Na pyrophosphate, pH 5.0. To each well was added approximately 5 ng of horseradish peroxidase (Sigma Chemical Co. Type VI). The blue color characteristic of TMB oxidation to the meriquinone began to appear immediately and intensified slowly; the reaction was allowed to proceed overnight at room temperature.

After approximately 12 hours of reaction, all wells contained in a dark blue solution of meriquinone. The wells containing citrate buffer also contained blue crystals of the citrate salt of the TMB meriquinone. The wells containing pyrophosphate also contained blue-violet crystals of the meriquinone pyrophosphate salt. The adsorbent strips which had been incubated in water contained very little color—no more than expected from soaking with the meriquinone solution. The strips which had been incubated in 0.7% polyacrylate were a uniform light (robin's-egg) blue. The strips which had been incubated in 1.0% dextran $SO_4$ were a uniform blue-violet. These differences were seen for all three kinds of adsorbent and for both incubation buffers, though strip staining was darker in citrate than in pyrophosphate.

Each strip was soaked for six hours at room temperature in 50 ml of 0.10M Na acatate, 10% ethanol, pH 5.0. The dextran sulfate strips lost essentially no color to the solvent. The DE81 and ET81 strips incubated in polyacrylate lost over half of their color to the solvent. The Zeta-Probe strips incubated in polyacrylwate lost much less than half of their color to the solvent. The water-incubated strips lost almost all of their color to the solvent. Mechanical abrasion of the strips which did not remove support material caused no significant loss of color. The nylon support was much more resistant to abrasion than the papers.

These results demonstrate several things.

(1) The cationic adsorbents have no intrinsic affinity for TMB meriquinone.

(2) After loading with either of two polymeric anions, all three cationic adsorbents bind easily visible amounts of the meriquinone, despite competition from buffer anions which form insoluble meriquinone salts.

(3) The meriquinone-polyanion complexes have characteristic colors, green-blue for polyacrylate and blue-violet for dextran sulfate, independent of the colors of the buffer-anion salts formed simultaneously in the same reaction mixture.

(4) The polyacrylate complex is not bound to the cationic adsorbents as tightly as the dextran sulfate complex. This effect is expected because polyacrylate is much less negatively charged than dextran sulfate.

(5) Nylon binds polyacrylate-meriquinone complex more tightly than the cationic papers do. This effect also is unsurprising, because polyacrylate and nylon are both much less hydrophilic than dextran sulfate and paper, and so might show some non-covalent affinity via hydrophobic interactions.

(6) The complex ions completely permeate the polymeric supports in such a way as to give the color great mechanical durability.

II. Neutral Adsorbents

The methods used in Part A with cationic adsorbents was repeated with two uncharged polymers manufactured in sheet form: nitrocellulose (Schleicher & Schuell, 0.45μ meter) and nylon 66 (MSI Corporation 0.45 μmeter Magna Nylon 66 membrane filters). The cationic nylon membrane, Zeta-Probe, was repeated as a positive control. The only procedural change from Part A was to use 1–2 ng horseradish peroxidase per 8 ml well instead of 5 ng, so that meriquinone was generated more slowly. This change caused almost all of the meriquinone to be adsorbed to the strips rather than deposited as the citrate or pyrophosphate salt, presumably because most of the meriquinone had a chance to diffuse to a strip before its concentration grew sufficiently to cause precipitation.

The Zeta-Probe strips performed as before. Regardless of buffer anion, membranes pre-treated with dextran sulfate became blue-violet; membranes pre-treated with water retained no color after less than an hour's soaking in $10^{-1}$M Na acetate, 10% ethanol, pH 5.0. None of the color of the poly-anion treated membranes could be removed by overnight soaking in this solvent. The MSI uncharged nylon membrane performed identically to Zeta-Probe in all respects. The nitrocellulose membranes differed from the others in one major respect: a uniform green color was found on all membranes regardless of pre-treatment or buffer ion. Dextran sulfate did not give a blue-violet deposit, and the water-treated membranes were almost as dark as those which had seen poly-anion.

There are two major conclusions to be drawn from this experiment:

(1) The polymeric anions have sufficient affinity for nominally neutral membranes that adsorbents need not be restricted to cationic polymers.

(2) The TMB meriquinone has enough affinity for the most hydrophobic membrane tested, nitrocellulose, that polymeric anion may not always be necessary. However, the color formed on binding to nitrocellulose is not as dark as those seen on other membranes treated with polymeric anions.

These experiments do not permit choice of the best adsorbent and immobilizing ion for actual analytical procedures because no effort was made to operate near the optical detection limit. The ability of meriquinone to bind to nitrocellulose without polymeric anion does not imply that this interaction is tight enough or that the color is dark enough to be analytically useful. As in Part A, the color formed on membranes completely resisted mechanical removal, regardless of membrane composition.

This example provides a model for a wide array of analytical applications of the ionic properties of the TMB meriquinone, wherein this colored indicator of oxidative (especially peroxidative) activity is immobilized and localized via complexation with polymeric anions which permeate and are strongly bound to polymeric supports. The interactions immobilizing the polymeric anions may be ionic or hydrophobic or both, depending on the choice of polymeric anion and of support. Such complex ions may have a strong advantage over crystalline meriquinone salts, in that they are bound to the support much more tightly than are crystals, in a way which defies mechanical disruption.

EXAMPLE 4

Immobilization on Ion Exchange Resins of the Meriquinone of TMB and of Its Complex with Dextran Sulfate Solutions of the meriquinone of TMB and of the meriquinone complex with dextran sulfate were made by incubating approximately 1 $\mu$g of horseradish peroxidase (Sigma Chemical Company Type VI) at room temperature with 50 ml volumes of 0.2 mg/ml TMB, 0.0015% $H_2O_2$, 10% ethanol in each of the following buffers: 0.10M sodium acetate, 1.0% dextran sulfate, and 0.10% dextran sulfate. All buffers were adjusted with NaOH or HCl to give final pH values of 5.0 after the ethanol was added. The dextran sulfate was from Pharmacia Fine Chemicals (catalogue number 17-0340-02). After 12 hours reaction the acetate reaction mixture was dark blue with no crystals and the dextran sulfate reaction mixture was violet-black with no crystals. The preparations were stored at 5° C. until use; during this incubation, some crystals formed in the acetate; none devellopped in either dextran sulfate solution.

Approximately 0.5 ml beds of the following ion-exchange polymers were poured at room temperature in polypropylene disposable columns (Isolab Quik-Step): Whatman carboxymethyl cellulose (CM-C), carboxymethyl Sepharose (CM-S, Pharmacia Fine Chemicals), sulfopropyl Trisacryl (SP-T, LKB Instruments), diethylaminoethyl cellulose (DEAE-C, Whatman), and diethylaminoethyl Sepharose (Pharmacia Fine Chemicals DEAE-S). (Sepharose is a beaded agarose. Trisacryl is an especially hydrophilic analogue of polyacrylamide, also cast in bead form.) Three columns were prepared of each ion exchange, one for each of the soluble meriquinone preparations described above. After each bed was washed with at least 5 ml of 0.10M sodium acetate, 0.001M EDTA, 10% ethanol, pH 5.0, aliquots of each of the three meriquinone preparations were added to separate columns of each exchanger and allowed to penetrate the columns; then 2-10 ml volumes of the column equilibration buffer were used to wash any unbound meriquinone through each column.

Three serial aliquots of meriquinone in acetate buffer were applied to a column containing each ion exchanger: 0.10 ml, 0.50 ml, and 5.0 ml. For each of the cation exchangers (CM-C, CM-S, and SP-T), all of the blue color stuck in a very tight band at the top of the column. Less than 20% of the column capacity was used in each case. No color should be washed from the column in 0.10M Na acetate, 10% ethanol, pH 5.0. For each of the anion exchangers (DEAE-C, DEAE-S), all of the color washed directly through the column. A few crystals of the acetate salt of the meriquinone which had formed during storage at 5° C. were trapped mechanically at the top of the columns and had to be dissolved by swirling in the elution buffer. There was no sign of retention by ion-exchange interactions.

One 0.10 ml aliquot of meriquinone in 1% dextran sulfate was applied to a column of each ion exchanger. The violet color was washed through the cation exchangers by 2-3 ml of solvent with no obvious retardation or retention. The columns were left with very pale green colors, suggestive of slight competition between the ion exchanger and the dextran sulfate for meriquinone. CM-C and SP-T retained more green color than CM-S; this fact suggests that the former have higher exchange capacities or affinities for cations than the latter. The violet color was completely retained in a band at the top of the DEAE-C column but was incompletely retained by the DEAE-S column. This fact suggests that DEAE-C has a higher exchange capacity than DEAE-S.

Two serial aliquots of meriquinone in 0.1% dextran sulfate were applied to and washed through a column containing each exchanger: 0.10 ml and 0.40 ml. Again, all of the violet color washed through each cation exchanger, leaving a pale green color which was weaker in the CM-S than in the Cm-C or SP-T. The DEAE-C column retained all of the applied violet color, even after washing with 5 ml of 0.10M Na acetate, 10% ethanol, pH 5.0. The DEAE-S column retained all of the violet color in the 0.10 ml aliquot of meriquinone, but passed about half of that in the following 0.40 ml aliquot. Once more the substituted cellulose appeared to have higher exchange capacity than the substituted Sepharose.

These results are in complete agreement with the following structural models for the meriquinone and its complex with dextran sulfate. The meriquinone is a cation which forms a very soluble acetate salt. As a cation, it binds well to cation exchangers but not to anion exchangers. The tightness of binding supports the idea that the meriquinone is a dication. It forms a tight complex with the polymeric anion, dextran sulfate. At the molar ratios of meriquinone and polymeric anion used here, there is an excess of negative charges on the dextran sulfate, so that the complex ion cannot precipitate, binds tightly to anion exchangers, and does not bind to cation exchangers. However, the net charge of the complex ion is so much higher than that of the meriquinone that ion exchange adsorbents with similar ionic capacity will bind much less pigmentation when it is attached to dextran sulfate than when it occurs as the uncomplexed meriquinone. Because the ionic interaction between meriquinone and polymeric anion is reversible, some meriquinone can escape the complex and bind to a cation exchanger when the complex is passed through the latter. (The green color, indicative of partial dissociation of the meriquinone into TMB and the quinone diimine, is commonly seen when the meriquinone is present at low concentration in the absence of excess TMB.)

This experiment provides a model for a wide array of analytical applications of the ionic properties of the TMB meriquinone, wherein this colored indicator of oxidative (especially peroxidative) activity is immobilized and localized on ion-exchange polymers. It may be directly bound to negatively charged supports or complexed to a polymeric anion which binds to positively charged supports. In this example, such complexation occurred before immobilization. In such an application, too great an excess of polymeric anion should be avoided. Otherwise, the limited exchange capacity of the support may prevent all of the meriquinone from being bound. In Example 3, complexation of meriquinone with polymeric anion occurred after the latter had been adsorbed to the support. Such a strategy has two advantages. It lessens the likelihood of limitation by support binding capacity for polymeric anion. It also is less likely to permit diffusion of the meriquinone away from site of formation. This latter feature is important for many analytical applications, where localization of peroxidative activity is as important as the sensitivity-enhancing concentration of color in a small region.

EXAMPLE 5

Use of TMB to Visualize Nucleic Acid Hybridization on Genomic Southern Blots

I. Preparation of DNA Probes

The synthesis of N-biotinyl, N'-(4'-methylene trioxsalen)-3,6,9-trioxa-undecane-1,11-diamine and of 1-(biotinylamino)-13-(4,5',8-trimethylpsoralen-4'-yl)-3,6,9,12-tetraoxa-tridecane are described in U.S. Pat. No. 4,582,789 issued Apr. 15, 1986, the entire disclosure of which is incorporated herein by reference. In addition, that patent discloses the biotinylation of DNA using these compounds to prepare HLA-DPα probes.

II. Hybridization of Probes to HLA Insert

Two μg of human DNA were digested with BglII, electrophoresed through 1% agarose minigels, and transferred to a Genatran 45 charge-modified nylon membrane (Plasco, Inc.) as described by Southern ((1975) *JMB* 98:503–517). In some lanes biotinylated DNA molecular weight markers (described above) and/or a positive control consisting of genomic DNA isolated from a homozygous typing cell line WT51 (Tissue Antigen Laboratory, Imperial Cancer Research Fund, London, England) digested with the same restriction endonuclease were included. After transfer to the membrane the filter-bound human DNA was fixed on the membrane using the standard procedure with base, neutralization with Tris-HCl buffer and baking at one hour or longer at 80° C. in a vacuum oven, as described by Southern, supra. The membrane was then wetted with distilled water for one minute, and placed in a sealable pouch. A prehybridization solution was then added to the membrane consisting of 5×Denhardt's solution with 50% formamide, 5×SSPE, 0.5% (w/w) SDS, 0–10% (preferably 5%) dextran sulfate, and 150 μg/ml denatured herring sperm DNA (available from Sigma). The membrane was incubated with the solution for 2–4 hours at 42° C. Then a hybridization solution was added to the membrane in an amount of 0.1 ml solution/cm² membrane consisting of 5×Denhardt's solution with 50% formamide, 5×SSPE, 0.5% (w/v) SDS, 0–10% dextran sulfate, 150 μg/ml denatured herring sperm DNA (sheared before denaturation by repeated passage through a 25 gauge hypodermic needle, and 50–200 ng per ml of either probe. The membranes were incubated overnight (about 14–18 hours) at about 42° C. The membranes were then washed three times for five minutes each with shaking at room temperature in 2×SSPE, 0.5% Tween 20 and three times at 60° C. for five minutes with shaking in 0.2–0.3×SSPE, 0.5% Tween 20 to produce a probe-hybridized Southern blot.

III. Horseradish Peroxidase-Streptavidin (HRP-SA) Conjugate Preparation

Horseradish peroxidase (HRP) quantities were calculated from an assumed molecular weight of 40,000 g/mole and an assumed $A_{402, 1 cm, 0.1\%}$ of 2.5. Streptavidin (SA) quantities were calculated from an assumed molecular weight of 60,000 g/mole and an assumed $A_{280, 1 cm, 0.1\%}$ of 3.0.

To 40 mg of HRP (Sigma Chemical Co. Type VI), dissolved in 1.9 ml of 0.10M Na phosphate, pH 7.5, and dialyzed at 4 C against the same buffer, were added 0.14 ml of 14 mg/ml mal-sac-HNSA ester dissolved in the same buffer. [mal-sacHNSA ester (where HNSA=4-hydroxy-3-nitrobenzene sulfonic acid) is the subject of copending patent application Ser. No. 839,447 filed Mar. 10, 1986, the disclosure of which is incorporated herein by reference. In addition, Bhatnagar et al., *Peptides: Synthesis-Structure-Function*, ed. by D. Rich et al. (Rockford: Pierce Chemical Co., 1981), p. 97–100, describes a method for preparing DNP-SAC and TNP-SAC esters using as the acid N-maleimido-6-aminocaproic acid that may be used to prepare the mal-sac HNSA ester. The HNSA ester is also described by Nitecki et al., *High-Technology Route to Virus Vaccines* (American Society for Microbiology: 1986) in a chapter entitled "Novel Agent for Coupling Synthetic Peptides to Carriers and Its Application".] This mixture was incubated for 105 min at room temperature, desalted on a 10.5 ml column of Sephadex G-25 equilibrated with 0.010M Na phosphate, 0.005M EDTA, pH 6.0, and dialyzed at 4 C. against three 200 ml volumes of the same buffer. The maleimide content of the derivatized HRP was assayed by diluting 0.2 mg in 0.50 ml of 0.10M Na phosphate, 0.005M EDTA, pH 7.0, adding 20 μl of 0.74 mM cysteine, incubating 5 min at room temperature, adding 33 μl of 4 mg/ml 5,5'-dithiobis(2-nitrobenzoic acid), incubating 2 min at room temperature, and measuring $A_{412}$ in a spectrophotometer. The difference in $\Delta A_{412}$ between this reaction and one for a control mixture to which no protein had been added, divided by the $\Delta\epsilon_{412}$ of $1.36 \times 10^4 M^{-1} cm^{-1}$, gave the molarity of maleimide in the diluted HRP.

Fifteen mg of SA (Sigma Chemical Co.) were dissolved in 1.5 ml of 0.10M Na phosphate, pH 8.0, dialyzed at 4 C. against three 200 ml volumes of the same buffer, and diluted to a concentration of 6 mg/ml in the same buffer. S-acetyl mercaptosuccinic anhydride (SAMCA, Aldrich Chemical Co.) was dissolved in dimethyl formamide at a concentration of 8.8 mg/ml. To 12 mg of dialyzed SA were added 125 μl of this SAMCA solution with gentle stirring at room temperature over about 1 min. After 30 min incubation at room temperature, the reaction mixture was desalted on a 10.5 ml column of Sephadex G-25 equilibrated with 0.10M TrisCl, 0.005M EDTA, pH 6.8. The pooled protein was dialyzed at 4 C. against three 20 ml volumes of the same buffer. The dialyzed derivatized SA was concentrated at room temperature to 10 mg/ml in an Amicon 8 MC ultrafiltration device with a YM10 membrane. Ten mg of concentrated SA were mixed with 0.5 ml of 1.0M hydroxylamine in 0.10M TrisCl, 0.005M EDTA, pH 6.8 with gentle stirring. After a 30 min incubation at room temperature, the SA was desalted on a 10.5 ml column of Sephadex G-25 equilibrated with 0.010M Na phosphate, 0.005M EDTA, pH 6.0. A small aliquot of the pooled protein peak was assayed for reactive thiols by measuring the change in $A_{412}$ after adding 5,5'-dithiobis(2-nitrobenzoic acid) to a concentration of 1 mM in 0.10M Na phosphate, pH 8.0.

The assays of maleimide on HRP and of thiols on SA were done immediately before mixing them to perform the coupling reaction. Then 3.95 ml of 13.0 mg/ml HRP bearing 0.67 maleimides/HRP were mixed in an ice bath with 2.47 ml of 4.19 mg/ml SA bearing 9.66 thiols/SA. After a 24 hr incubation at 5 C., the unreacted thiols were blocked by adding 0.47 ml of 4.6 mg/ml N-ethyl maleimide dissolved in 0.010M Na phosphate, 0.005M Na EDTA, pH 6.0 and incubating at room temperature for 30 min.

The reaction mixture was fractionated into conjugate pools of different mean HRP/SA molar ratio, separated from unreacted HRP, by gel filtration chromatography on a 2.5×80 cm column of Ultrogel AcA 44 (LKB Instruments) at 4 C. in 0.10M Na phosphate, pH 6.8, at a flow rate of 3 cm/hr. The composition of the conjugate pools was estimated spectrophotometrically from the $A_{402}/A_{280}$ ratio and quantitated accurately by densitometric scanning of a Nuclear Fast Green stained 5-20% gradient SDS-PAGE gel, run under reducing conditions. Approximately 10 mg of a mixed 2-mer and 3-mer (species containing 2 HRP:SA and 3 HRP:SA) and 5 mg of fairly pure 1-mer were recovered from gel filtration. These conjugate pools, containing no detectable uncoupled SA or HRP, were stored at 4 C. for many months with negligible loss of protein or HRP catalytic activity. The mixture of 2-mer and 3-mer was used preferentially in detecting biotinylated DNA probe hybridized to human genomic Southern blots, but 1-mer gave almost the same intensity of staining.

IV. Probe Detection

All operations took place at room temperature. The probe-hybridized Southern blot from section II was rinsed once in 35 ml of phosphate-buffered saline (2.7 mM KCl, 136.9 mM NaCl, 1.5 mM $KH_2PO_4$ and 8 mM $Na_2HPO_4$) to which had been added 0.1M NaCl and 5% Triton X-100 (Buffer A). After 5 min of gentle agitation, the rinse solvent was replaced with Buffer A containing HRP-SA at a concentration such that the component HRP was present at 0.3 μg/ml. The amount of Buffer A plus HRP-SA was 0.5–1 ml/cm² of membrane. Conjugate was incubated with the membrane for 20 min with or without agitation. Then the membrane was removed to a clean Petri dish and rinsed 5 times with 45 ml volumes of Buffer A to which had been added 0.15M 1,1-diethylurea and 1% Na dextran sulfate (Buffer B). These 5-minute washes with gentle agitation were followed by one 5-minute wash with gentle agitation in 10 mM Na citrate, 10 mM Na EDTA, pH 5.0 (Buffer C) containing 0.1 mg/ml TMB. At this point, the membrane was incubated undisturbed in 50 ml of Buffer C containing 0.1 mg/ml TMB and 0.0014% $H_2O_2$. Over 15–60 minutes, dark blue bands developed on the membrane wherever biotinylated DNA was located—either biotinylated λ DNA fragments used as molecular weight standards or biotinylated probe hybridized to targeted DNA. When satisfactory contrast was obtained, the substrate solution was drained from the membrane, which was rinsed four times for five minutes each with 50 ml water with gentle agitation. The washed membrane was stored in water in a sealed test tube or plastic bag in the dark at room temperature, 4° C., or −20° C.

When 2 μg of DNA from a human subject bearing the DQα HLA gene were subjected to the analysis just described, and the Southern blot was hybridized with a circular DNA probe containing a DQα insert and covalently tagged with 0.05 moles of BP3 per mole of DNA base pair, the pattern obtained after HRP-TMB visualization contained two bands of equal intensity, one at 2.3 kilobases and one at 4.7 kilobases, relative to biotinylated molecular weight standards on the same blot. When citrate in buffer C was replaced by pyrophosphate or sulfate, ions which Example 1 shows to give meriquinone salts with much darker colors than citrate does, the Southern blot color was unchanged. When dextran sulfate was removed from the hybridization protocol, no permanent pattern was formed on the Southern blot. When neutral nylon membranes, rather than cationic charge-modified membranes like Zeta-Probe (Example 3) or Genatran (this Example), were used to make the Southern blot, the meriquinone-stained band pattern also was very labile and tended to diffuse from the surface of the membrane into solution, if but only if dextran sulfate was not added to Buffer B. These observations suggest that in Southern blots prepared as described above, some of the dextran sulfate used in the hybridization step binds to the cationic membrane and permits immobilization of the meriquinone formed during probe detection. Addition of dextran sulfate during the washes after conjugate incubation can compensate for poor retention of dextran sulfate from hybridization.

EXAMPLE 6

Use of TMB to Visualize Immuno Blots

I. Immunoblot Preparation

The eukaryotic cell lines noted below were grown to near confluence in DME tissue culture media supplemented with 5% fetal calf serum. Whole-cell extracts were prepared by aspirating the tissue culture medium, and adding lysis buffer (0.20M LiCl, 0.020M Tris Cl, 0.001M EDTA, 0.5% Nonidet P-40, and 0.05% aprotinin, pH 8.0) directly to the tissue culture plates. The resulting clear solution was mixed with an equal volume of 5% SDS, 1M dithiothreitol, 10% glycerol, 0.005% bromphenol blue, 0.125M Tris Cl, pH 6.8. Fifty μl samples were fractionated by SDS-PAGE in a 3.5×4 cm 12% polyacrylamide gel (Laemmli (1970), *Nature* 227: 680–685).

Immunoblotting of the gel onto nitrocellulose (Schleicher and Schuell, 0.45μ meter) was performed in a Bio-Rad Trans-blot cell at 35 V for one hour at room temperature essentially according to published methods (Towbin et al. (1979) *Proceedings of the National Academy of Sciences, USA* 76: 4350–4354; Bittner et al. (1980) *Analytical Biochemistry* 102: 459–471; Burnette et al. (1981) *Analytical Biochemistry* 112: 195–203). Following transfer nonspecific antibody binding sites on the nitrocellulose were blocked by incubation for 30 minutes at room temperature with gentle agitation in 250 ml of 5% nonfat dry milk (Carnation), 1% ovalbumin (Sigma Chemical Co. Grade III), 1M glycine. Then the blot was washed three times with gentle agitation at room temperature for five minutes each in 250 ml volumes of 0.1% nonfaty dry milk, 0.1% Tween 20, 0.15M NaCl, 17.5 mM $KH_2PO_4$, 14.74 mM NaOH, pH 7.4, and incubated with gentle agitation for three hours at room temperature in 5 ml of a 1/400 dilution in the preceding buffer of rabbit antiserum against a synthetic oligopeptide with the amino acid sequence corresponding to amino acids 29 to 44 of the ras oncogene. After washing three times as described above, the blot was incubated for one hour at room temperature with 5 ml of a 1/3000 dilution of goat anti-rabbit IgG conjugated to horseradish peroxidase (this conjugate supplied by Bio-Rad Laboratories) and washed again three times as above.

II. TMB Detection of Immobilized HRP Immunoconjugate

The immunoconjugate-treated blot was soaked at room temperature without agitation for five minutes in 50 ml of 0.10M Na fumarate, 0.0001M EDTA, pH 4.8 and then for 30–60 minutes in 50 ml of freshly prepared 0.10M Na fumarate, 0.001M EDTA, 5% ethanol, 0.1 mg/ml TMB (Miles Laboratories), 0.00075% $H_2O_2$. When the pattern had reached the desired degree of contrast between specifically stained bands and background, the blot was soaked for 30–60 minutes in 50 ml of 0.10M Na fumarate, 0.001M EDTA, pH 4.8, before drying at room temperature between two sheets of blotting paper.

III. 3,3'-Diaminobenzidine (DAB) Detection of Immobilized HRP Immunoconjugates

The immunoconjugate-treated blot was incubated without agitation at room temperature for 10 minutes in 50 ml of 0.1M Tris Cl, pH 7.4, containing 25 mg of DAB and 0.03% $H_2O_2$. After 15 minutes of washing in circulating distilled water, the blot was dried between two sheets of blotting paper.

FIG. 3 compares the use of TMB and DAB to visualize specific polypeptides from whole-cell extracts of eukaryotic cells after immunoblotting. Panels 1 and 2 were stained via TMB oxidation. Panel 3 was stained via DAB oxidation. Panel 4 was stained for protein with Amido Black. All four panels represent immunoblots prepared identically except for the sample subjected to SDS-PAGE. Panel 4 represents a commercial mixture of proteins serving as molecular-weight markers (Bio-Rad Laboratories, low-MW marker mixture). The molecular weight values are (from top to bottom); 92, 66, 45, 31, 20, and 14 KD, respectively.

Panel 1 represents whole-cell extracts from a mouse cultured cell line, K-balb (left lane) and a rat cultured cell line, Kp6 (right lane), probed on the immunoblot with an antiserum (onc 29) prepared by inoculation of a rabbit with a synthetic polypeptide (amino acids 29-44 of the 21 KD protein coded by the ras oncogene) conjugated to keyhole limpet hemocyanin and subsequently blocked by incubation with the same synthetic polypeptide conjugated to bovine serum albumin. Panels 2 and 3 are duplicate immunoblots of whole-cell extracts from three cell lines: "Hs242" (left lane), K-balb (center lane), and Kp6 (right lane), probed with the same anti-p21 (ras) rabbit antiserum used for Panel 1, unblocked by the serum albumin-coupled antigenic oligopeptide. K-balb and Kp6 are described by Clark et al. (1985) *Proc. Natl. Acad. Sci. (USA)* 82: 5280-5284. "Hs242" is a murine cell line created by transformation of the NIH 3T3 line with the activated ras p21 gene from a cell line derived from a human lung adenocarcinoma (Yuasa et al. (1983) *Nature* 303: 775-779).

Comparison of Panels 2 and 3 of FIG. 3 shows that TMB visualization is two to four-fold more sensitive than DAB visualization, for immunoblots. The naturally occurring polypeptide, p21. identified by the rabbit antiserum, onc 29, has a molecular weight of 21 KD according to the immunoblot, and is not detected when the antiserum has been blocked by the immunogenic shorter polypeptide used to elicit the anti-p21 antibody (Panel 1).

The above examples show improved performance of Western blots and Southern blots when TMB is used as a horseradish peroxidase substrate under conditions where the added anion helps to localize the developed color. This technology has permitted attainment of the DNA probes detection limit goal on human genomic Southern blots and identification of the ras p21 antigen on Western blots of cell extracts.

EXAMPLE 7

Detection of HRP in Solution by Filter-Trapping the Fumarate Salt of The Meriquinone of TMB A fumarate-buffered HRP assay solution was prepared by mixing 50 μl of 0.60M $H_2O_2$ (in water), 50 μl of 0.060M 3,3',5,5'-tetramethylbenzidine (TMB, in 95% ethanol), 40 μl of 0.25M sodium EDTA, pH 7.2, 1.00 ml of 0.100M sodium fumarate, pH 3.60, and 9.00 ml of deionized water. The final solution was 3.0 mM $H_2O_2$, 0.31 mM TMB, 1.0 mM EDTA, 10 mM fumarate, pH 3.92. Stock HRP solutions were prepared in 0.10M NaCl, 1.0 mM Na phosphate, pH 6.0 to be 22 ng/ml or 0.43 ng/ml in HRP, shortly before assay, HRP-catalyzed oxidation of TMB by $H_2O_2$ was initiated by adding 20 or 2.0 μl of 22 ng/nl HRP or 20 or 10 μl of 0.43 ng/ml HRP to 1.00 ml of the assay solution at 25° C. At the two higher HRP concentrations (11 and 1.1 pM in the cuvette), the generation of meriquinone was monitored at 652 nm in an HP8450A spectrophotometer for five minutes. At the two lower HRP concentrations (0.22 and 0.11 pM in the cuvette), the reaction was followed for 30 minutes. At the end of each reaction interval, replicate 100 μl volumes of reaction mixture were spotted on a Nuclepore polycarbonate filter (3 μm pore size) and dried by gentle suction to give deposits 3-4 mm in diameter.

The kinetic traces for these reactions showed the initial slopes expected for the respective HRP concentrations. However, after an interval of 1-10 minutes (increasing as the HRP concentration was lowered), the traces leveled off abruptly, often showing a sharp dip. This behavior, uncharacteristic of assays performed in buffers which do not readily precipitate the meriquinone, such as citrate and acetate, indicates the nucleation of product crystals, in this case the fumarate salt of the meriquinone. After nucleation, replicate traces diverge considerably because of the random nature of crystal nucleation and growth. For each of the four reactions, 3 μm filtration of 100 μl volumes of reaction mixture left blue deposits, clearly visible to the unaided eye, which were stable during standing for over a week at room temperature exposed to ambient visible light (from fluorescent fixtures).

Table V summarizes the results from the reactions. The initial velocity was transformed from units of absorbance per time to reciprocal time (turnover number) by dividing by the meriquinone extinction coefficient, $3.9 \times 10^4$ $M^{-1}cm^{-1}$, and by the HRP concentration. The uniformity of the turnover number over two orders of magnitude of HRP concentration and the fact that these turnover number values equaled those seen in non-precipitating buffers indicate that the only effect of fumarate is on product solubility. The transition time is the time to crystal nucleation. These data show that when the presence of HRP is monitored visually by observing the crystals of meriquinone fumarate salt which can be trapped by a 3 μm filter, the HRP detection limit in 100 μl of reaction mixture would be below $1.1 \times 10^{-16}$ moles of five minutes of reaction and below $1.1 \times 10^{31\ 17}$ moles for 30 minutes of reaction. The $A_{652}$ of the 30 minute reaction mixture for 0.11 pM HRP was below 0.03, the approximate visual threshold, so that filtration trapping served to concentrate the signal to improve visibility. As some blue color was observed to penetrate these ultra-thin straight-channel filter membranes, additional sensitivity could be obtained by using a smaller pore size, a depth filter, or an anionic membrane. In addition, a white membrane would offer sharper visual contrast than the slightly yellow, translucent, polycarbonate. The transition time has a very shallow HRP concentration dependence, so that even lower HRP concentrations are unlikely to require assay times longer than 30 minutes in order to permit crystallization to occur. The transition time probably could be lowered by adding anionic latex microspheres which might serve to nucleate crystallization.

This experiment is a model for the use of precipitation of the TMB meriquinone by effective anions as a method of trapping the HRP reaction product for visual detection in rapid enzyme immunoassays. These analyses, which are becoming popular in clinical diagnostics, follow a general format in which a body fluid or extract of a body fluid is incubated with a capture surface and with an enzyme-tagged probe antibody specific for the analyte of interest, filtered and washed to remove extraneous components of the test sample and excess probe conjugate, incubated with enzyme assay buffer, and, in those cases where the colored enzyme reaction product is insoluble or immobilizable, filtered and washed again to end the enzymatic reaction and limit background development. The capture surface may be the filter membrane itself or particles suspended in the fluid over the membrane, and may bind the analyte by chemisorption or be derivatized with an antibody or other binding protein with some specificity for the analyte. In any of these cases, the enzyme detection step is very much the same, and the colored product must be trapped in some fashion if filtration and washing is to be used to stop the reaction and preserve the signal.

TABLE V

Kinetics of TMB Oxidation by $H_2O_2$ and HRP in pH 3.9 Fumarate-EDTA Buffer
Reactions Performed in 0.31 mM TMB, 3.0 mM $H_2O_2$, 10 mM Na Fumarate, 1 mM EDTA, pH 3.92 at 25° C.

| [HRP] (M × $10^{12}$) | $V_{initial}$ $WA_{652}S^{-1}$ | $S^{-1}$ | Transition Time (Min.) | $A_{652}$ at Transition | Moles HRP in 100)l |
|---|---|---|---|---|---|
| 11 | $4.2 \times 10^{-3}$ | 9800 | 1–2 | 0.25–0.50 | $1.1 \times 10^{-15}$ |
| 1.1 | $4.1 \times 10^{-4}$ | 9600 | 3–4 | 0.08 | $1.1 \times 10^{-16}$ |
| 0.21 | $8.0 \times 10^{-5}$ | 9800 | 10 | 0.04 | $2.1 \times 10^{-17}$ |
| 0.11 | $4.4 \times 10^{-5}$ | 10300 | 10 | 0.025 | $1.1 \times 10^{-17}$ |

EXAMPLE 8

Controlling the Solubility of the Meriquinone of TMB with Ionic Strength

The insoluble dextran sulfate salt of the TMB meriquinone was made in two steps. First the soluble meriquinone was made by adding 5.0 ml of 2.0 mg/ml TMB (in 95% ethanol), 25)l of 3% $H_2O_2$ (in $H_2O$), and 20)l of 20 mg/ml HRP (in phosphate-buffered saline) to 45.0 ml of 0.010M Na acetate buffer pH 4.81. The final solution, pH 5.02, was 0.83 mM in TMB and 0.44 mM in $H_2O_2$; it turned deep blue within seconds. Then, after incubation at room temperature for at least 30 minutes, 800–850)l of 1% dextran sulfate (in water; 500 kD dextran sulfate from Pharmacia) were added to form instantaneously a deep violet suspension which settled over 30 minutes at room temperature to leave a colorless supernatant. The sediment was harvested by centrifugation and washed several times with deionized $H_2O$ before storage at 4° C.

To study the ionic strength dependence of meriquinone solubility, sodium acetate buffers of pH 4.96–5.02 were made with total acetate concentrations of 0.010, 0.025, 0.050, 0.100, 0.200, and 0.400M. At this pH the ionic strength values should be 64% of the acetate concentrations. To a 2 ml volume of each buffer was added approximately 10 mg of solid TMB and 5 mg of damp meriquinone-dextran sulfate salt. These mixtures were Vortex mixed for a total of about four minutes each at 23° C. before centrifuging and carefully removing the supernatant solutions with a Pasteur pipet. The 260–800 nm spectra were recorded in an HP 8450A spectrophotometer. Mixing, spinning, and scanning were repeated twice to give a total of three sets of absorbance values to check for equilibration. The absorbance values either remained constant or declined somewhat with repeated measurement, indicating that the first mixing sufficed to reach equilibrium.

Meriquinone solubility was approximately proportional to ionic strength for acetate concentrations up to 0.4M (ionic strengths up to 0.26), showing a fifty-fold increase from 0.01 to 0.4M acetate. At acetate concentrations of $10^{-2}M$ or less, dissolved meriquinone was barely detectable at 652 nm ($A_{652} < 0.008$) when it was in equilibrium with a salt containing charge-equivalent amounts of meriquinone and dextran sulfate. Such a low concentration is visually undetectable. The acetate concentration dependence of TMB solubility was also measured in the same way as meriquinone solubility, except that the meriquinone salt was omitted from the incubations and dissolved TMB was monitored at 285 nm. In this case, solubility showed a gentle and linear decline with increasing acetate, totaling 15% from 0.01 to 0.4M acetate. In 0.4M acetate at pH 5.0, the solubility of the meriquinone dextran sulfate salt almost equalled that of TMB.

Acetate was chosen to control ionic strength because the TMB acetate salt was already known to be very soluble, so that precipitation of the acetate salt was not expected to interfere with the salt dependence of the solubility of the meriquinone salt. The strong salt concentration dependence of the meriquinone solubility is consistent with the ionic nature of the interaction between meriquinone dication and polyanion. The slight decline in TMB solubility with increasing ionic strength is consistent with the molecular nature of the crystal of TMB, a relatively hydrophobic molecule. These data have obvious practical consequences. The washing of assays visualized with TMB, $H_2O_2$, and peroxidase or some other oxidation catalyst should be done at very low ionic strength to facilitate the removal of excess TMB and minimize the loss of signal through dissolution of the immobilized meriquinone. Often water should suffice as a wash solvent. On the other hand, there may be applications where it is desired to remove the signal generated by one probe in order to test a sample with a probe of different specificity. In that case, a wash in high ionic strength should suffice to remove all the meriquinone without subjecting the sample to harsh chemical conditions.

EXAMPLE 9

Detection of Sickle-cell and Normal Alleles of b-globin Locus

Two probes were made by cloning the 676 and 627 base pair Sau3AI fragments from the 1.9-kilobase pair BamHI fragment in the 5' part of the g-globin gene (in accordance with Fritsch et al. (1980) *Cell,* 19: 959–972) into the BamHI site of M13mp10 in accordance with Messing, J. (1983) *Meth. Enzymol.,* 101: 20–78. DNA probes were prepared by hybridizing the single-stranded M13 DNA containing the desired DNA insert to BamHI linearized M13 replication form essentially as described by Courage-Tebbe, U. and Kemper, B. (1982) *BBA,* 697: 1–5. The resulting M13 derivatives were photolabeled with a biotinylated psoralen derivative, N-biotinyl, N'-(4'-methylene trioxsalen)-3,6,9-trioxa-undecane-1,11-diamine as described in U.S. Pat. No. 4,582,789, supra. This resulted in probes labeled with 5–10 biotinylated psoralen moieties per 100 base pairs of double-stranded DNA as determined by measuring the absorbance at 333 nm as described by Cimino et al. (1985) *Ann. Rev. Biochem.,* 54: 1151–1193 and using a standard curve relating optical density and the incorporation of (3H) biotinylated psoralen.

Human DNA was purified from tissue culture cells or from blood by using a method described by Stetler et al. (1982) *PNAS,* 79: 5966–5979. Homozygous hemoglobin delta-beta deletion DNA was from GM2064 cells (Human Genetic Mutant Cell Repository, Camden, NJ), hemoglobin beta S/beta S DNA was from SC-1 cells described by Saiki et al. (1985) *Bio/Technology,* 3: 1008–1012, hemoglobin beta S/beta A DNA was from the blood of an individual with sickle-cell trait, and hemoglobin beta A/beta A DNA was from HL60 cells described by Collins et al. (1978) *PNAS,* 75: 2448–2462. DNA digestion with SauI and other restriction endonucleases was performed according to Maniatis et al. (1982) *Molecular Cloning* (Cold Spring Harbor Laboratory), pp. 382–389. To provide molecular weight standards that allow coincident nonisotopic detection, bacteriophage lambda BstEII fragments were labeled with biotinylated psoralen as described by U.S. Pat. No. 4,582,789, supra. The molecular weight standards and restriction digested DNA samples were fractionated by electrophoresis in neighboring lanes in 1% agarose gel in a buffer containing 0.04M Tris-acetate, 0.002M EDTA, pH 8.0. Blotting of the DNA samples to Genatran nylon membranes was carried out for 3–16 hours using 5×SSPE as described by Maniatis et al., supra (20×SSPE=3.6M NaCl, 200 mM NaH$_2$PO$_4$, 20 mM EDTA, pH 7.4).

The Genatran nylon membranes carrying the DNA samples were incubated in a prehybridization mixture consisting of 5×Denhardt's solution, 5×SSPE, 150 mg/ml of denatured herring sperm DNA, 0.5% sodium dodecyl sulfate, 5% sodium dextran sulfate, and 50% formamide at 42 C. for 2–6 hours and then drained. Next, 50 ng/ml of the first probe and 75 ng/ml of the second probe were added to a separate stock of the same mixture that had been prewarmed to 60 C. and then combined with the membrane for overnight incubation at 42 C. After hybridization, the nylon membrane was washed and a streptavidin-horseradish peroxidase conjugate and TMB were added under conditions as described in Example 5. Color development was for one hour.

The nonisotopic probe system distinguished the 1.14-kb band characteristic of the normal allele of the β-globin gene from the 1.34-kb fragment characteristic of the sickle cell allele in the human DNA tested, correctly identifying all homozygous and heterozygous genotypes.

Deposit

The deposit identified as the plasmid pDA318 in a MM294 host was deposited with the American Type Culture Collection (ATCC) of Rockville, MD 20852 USA under accession no. 39,917 on Nov. 8, 1984 pursuant to a contract between the ATCC and the assignee of this patent application, Cetus Corporation. The contract with ATCC provides for permanent availability of the progeny of this plasmid-containing host to the public on the issuance of the U.S. patent describing and identifying the deposit or the publications or upon the laying open to the public of any U.S. or foreign patent application, whichever comes first, and for availability of the progeny of this host to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the host on deposit should die or be lost or destroyed when cultivated under suitable conditions, it will be promptly replaced on notification with a viable culture of the same host.

In summary, the present invention provides a chromophoric reaction product, the use of which increases the sensitivity and lowers the detection limit of a wide range of analyses of oxidative activity. The product is deposited as an insoluble salt or immobilized complex at the site of catalytic activity in a gel or on the surface of a solid phase and does not fade over time or migrate, resulting in diffuse signals.

Those skilled in the art should note that the disclosure herein on particular embodiments of the present invention is exemplary only, and that various other alternatives, adaptations, and modifications may be made within the scope of the present invention. Accordingly, the present invention is not limited to the specific embodiments as illustrated herein, and is embodied in the claims appended hereto.

What is claimed is:

1. A composition of matter useful for visualization of oxidants, oxidation catalysts or peroxidative catalysts, comprising a complex of a polymeric anion and the meriquinone of a benzidine compound, the benzidine compound given by the structure

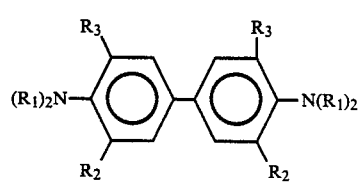

wherein R$_1$ is H and R$_2$ and R$_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, and wherein the complex can be isolated by immobilization or precipitation.

2. A composition of matter useful for visualization of oxidants, oxidation catalysts or peroxidative catalysts, comprising a solid salt of an anion and the meriquinone of a benzidine compound, the benzidine compound given by the structure

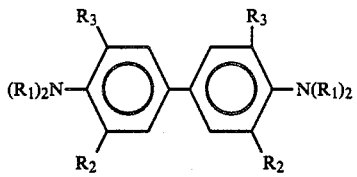

wherein $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, and wherein the anion is the conjugate base of an unsaturated or an aromatic organic acid.

3. The composition of claim 1 wherein the benzidine compound is 3,3′,5,5′-tetramethylbenzidine (TMB).

4. A composition of matter useful for visualization of oxidants, oxidation catalysts or peroxidative catalysts, comprising a solid salt of an anion and the meriquinone of a benzidine compound, the benzidine compound given by the structure

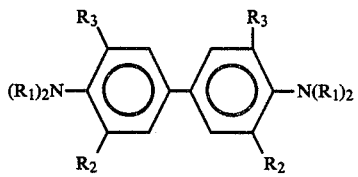

wherein $R_1$ is H and $R_2$ and $R_3$ are independently selected from the group consisting of —H, —F, —Cl, —Br, —C$_3$, —OCH$_3$, —(CH$_2$)$_n$CH$_3$, and —O—(CH$_2$)$_n$CH$_3$, where n is an integer of from 1 to 10, and wherein the anion is selected from the group consisting of maleate, oxalate, malonate, succinate, glutarate, fumarate, phthalate, isophthalate, terephthalate, malate, tartarate, pyrophosphate, formate, isocitrate, ethylenedinitrilotetra-acetate, 1,2,3,4-butane tetracarboxylate, benzoate, hemimellitate, trimellitate, trimesate, pyromellitate, mellitate and mesaconate.

5. A composition of matter useful for visualization of oxidants, oxidation catalysts or peroxidative catalysts, comprising a solid salt of the meriquinone of TMB and an anion selected from the group consisting of halide, nitrate, citrate, maleate, sulfate, oxalate, malonate, succinate, glutarate, fumarate, phthalate, isophthalate, terephthalate, malate, tartarate, pyrophosphate, formate, isocitrate, ethylenedinitrilotetra-acetate, 1,2,3,4-butane tetracarboxylate, benzoate, hemimellitate, trimellitate, trimesate, pyromellitate, mellitate and mesaconate.

6. The composition of claim 1 wherein the polymeric anion is selected from the group consisting of polyacrylate, polymethacrylate, carboxymethyl cellulose, sulfoethyl cellulose, polyphosphate, polyanethole sulfonate and dextran sulfate.

7. A solid phase or gel containing the composition of claim 1.

8. A polymer to which is adsorbed the composition of claim 1.

9. A process for visualizing material comprising an oxidation catalyst or a peroxidative catalyst, the process comprising contacting the material with a benzidine compound in an aqueous reaction medium at a pH of about 3 to 7 so that the benzidine compound is oxidized to a meriquinone derivative thereof, wherein said contacting is in the presence of an oxidant and an amount of an anion or polymeric anion effective to cause formation of a solid salt or immobilized or precipitated complex of the anion or polymeric anion and the meriquinone derivative, thereby forming a solid salt or immobilized or precipitated complex of said anion or polymeric anion, and visualizing any complex so formed, wherein the benzidine compound is given by the structure

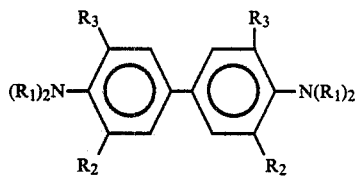

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, and wherein the concentration of dissolved meriquinone in equilibrium with said salt or complex ion is less than about $10^{-5}$M.

10. The process of claim 9 wherein the benzidine compound is TMB, the oxidant is a hydroperoxide, the pH is about 3.5–5.5, and the TMB is used at a concentration near its solubility at said pH of 3.5–5.5.

11. The process of claim 9 wherein the catalyst is a peroxidase attached to a nucleic acid or to a non-catalytic protein selected from the group consisting of an antibody, antigen, hormone-binding protein, carbohydrate, avidin, streptavidin, lectin, protease inhibitor, nucleic-acid-binding protein, and antibody-binding protein.

12. The process of claim 11 wherein said antibody-binding protein is an anti-antibody.

13. The process of claim 11 wherein the non-catalytic protein is an antibody which binds specifically to a virus, rickettsial, bacterium or eukaryotic cell.

14. The process of claim 11 wherein the non-catalytic protein is streptavidin.

15. The process of claim 11 wherein the nucleic acid comprises a nucleotide sequence which is complementary to a sequence from a chromosome of an organism.

16. The process of claim 9 wherein the material comprises or is bound to a nucleic acid.

17. The process of claim 16 wherein the visualization is achieved on a Southern blot, a Northern blot, a DNA dot blot or an RNA dot blot.

18. The process of claim 17 wherein the polymeric anion is dextran sulfate.

19. The process of claim 9, used to detect as analyte a protein selected from the group consisting of antibody, antigen and hemoprotein.

20. The process of claim 19 wherein the anion is pyrophosphate or a combination of fumarate and dextran sulfate.

21. The process of claim 19 wherein the protein is an antibody or antigen, and the visualization is achieved on a Western blot, an antigen dot blot, or an antibody dot-blot, in a cell culture, or in an enzyme immunoassay in aqueous solution or suspension.

22. The process of claim 9, used to detect an analyte selected from the group consisting of antigens, antibodies, nucleic acids, and carbohydrates, wherein said analyte is localized in tissue, cells or sub-cellular structures, and the visualization is achieved by histochemical or cytochemical staining.

23. The process of claim 9 wherein the oxidation catalyst or peroxidative catalyst material is localized on a solid phase or is contained in a gel or fluid.

24. The process of claim 23 wherein the solid phase comprises glass or a polymer selected from the group consisting of cellulose, nylon, fluorocarbon, polyester, agarose, acrylic ester, acrylic amide and polystyrene.

25. The process of claim 23 wherein the gel is selected from the group consisting of polyacrylamide, agarose, starch, or gelatin.

26. A process for visualizing an analyte selected from the group consisting of proteins, nucleic acids, carbohydrates and lipids, wherein the analyte contained in or on a test sample selected from the group consisting of a solid phase, a gel, a dissolved or suspended mixture containing complementary antibody and antigen, and a dissolved or suspended mixture containing single-stranded nucleic acids, which process comprises:
(a) contacting the test sample with an oxidation catalyst attached to a detecting compound capable of specifically binding to the analyte;
(b) incubating the test sample from step (a) under conditions whereby the detecting compound will analyte if it is present in the test sample;
(c) washing the test sample from step (b) to remove unbound detecting compound;
(d) adding to the washed test sample from step (c) a benzidine compound given by the structure

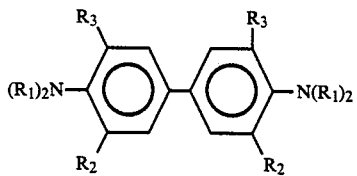

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10;
(e) subjecting the test sample to conditions under which the benzidine or substituted benzidine will oxidize to the meriquinone thereof in the presence of the oxidatively or peroxidatively active species, said conditions comprising a reaction temperature of 0° to 60° C. and an aqueous medium of pH 3 to 7;
wherein an amount of an anion or polymeric anion effective to cause formation of a solid salt or immobilized complex of the anion or polymeric anion with the meriquinone is added during one or more of steps (a)-(e), and wherein the concentration of dissolved meriquinone in equilibrium with said salt or complex ion is less than about $10^{-5}$M; and
(f) detecting the formation of a solid salt or immobilized complex of said anion or polymeric anion and said cationic meriquinone, wherein said formation indicates the presence or characteristics of the analyte.

27. The process of claim 26 wherein step (e) is carried out at a pH of about 3.5 to 5.5, the oxidation catalyst is horseradish peroxidase, the benzidine compound is TMB present at a concentration near its solubility at said pH of 3.5-5.5, and the oxidant is a hydroperoxide.

28. A process for visualizing an analyte selected from the group consisting of proteins, nucleic acids, carbohydrates and lipids, wherein the analyte is contained in or on a test sample selected from the group consisting of a solid phase, gel and liquid, which process comprises:
(a) contacting the test sample with a detecting compound capable of specifically binding to the analyte;
(b) contacting the test sample from step (a) with an oxidation catalyst attached to a moiety capable of specifically binding to the detecting compound;
(c) incubating the test sample from step (b) under conditions whereby the detecting compound will bind to the catalyst and to the analyte if it is present in the test sample;
(d) washing the test sample from step (c) to remove free detecting compound and catalyst;
(e) adding to the washed test sample from step (d) a benzidine compound given by the structure

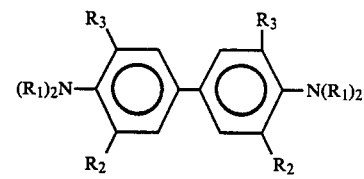

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10;
(f) subjecting the test sample to conditions under which the benzidine compound will oxidize to the meriquinone thereof in the presence of the analyte, said conditions comprising a reaction temperature of 0° to 60° C. and an aqueous medium of pH 3 to 7;
wherein an amount of an anion or polymeric anion effective to cause formation of a solid salt or immobilized complex of the anion or polymeric anion with the meriquinone is added during one or more of steps (a)-(f), and wherein the concentration of dissolved meriquinone in equilibrium with said salt or complex ion is less than about $10^{-5}$M; and
(g) detecting the formation of a solid salt or immobilized complex of said anion or polymeric anion and said cationic meriquinone, wherein said formation indicates the presence or characteristics of the analyte.

29. The process of claim 28 wherein step (g) comprises adsorbing the meriquinone to a surface bearing fixed negative charges, or trapping a solid salt of the meriquinone on a filter membrane.

30. A process for visualizing an analyte selected from the group consisting of an antigen, an antibody or a nucleic acid, contained in or on a solid phase using a Southern blot, a Northern blot, a DNA or RNA dot blot, a Western blot, an antigen dot blot or an antibody dot blot, which process comprises:

(a) contacting the solid phase with a peroxidase attached to a detecting compound selected from the group consisting of (i) an antibody capable of binding to the antigen, (ii) an antigen or anti-antibody capable of binding to the antibody, or (iii) a nucleic acid hybridization probe containing a single-stranded nucleotide sequence which is complementary to a sequence contained in the nucleic acid;

(b) incubating the solid phase from step (a) under conditions whereby the detecting compound will bind to the antigen, antibody or nucleic acid if it is present in the test sample;

(c) washing the solid phase from step (b) to remove unbound detecting compound;

(d) adding to the washed solid phase from step (c) a benzidine compound given by the structure

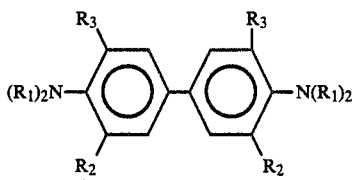

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10;

(e) subjecting the solid phase to conditions under which the benzidine compound will oxidize to the meriquinone thereof if the peroxidase is present, said conditions comprising a reaction temperature of 0° to 60° C. and an aqueous medium of pH 3 to 7 containing an amount of a hydroperoxide effective to oxidize the benzidine compound;

wherein an amount of an anion or polymeric anion effective to cause formation of a solid salt or immobilized complex of the anion or polymeric anion with the meriquinone is added during one or more of steps (a)–(e), and wherein the concentration of dissolved meriquinone in equilibrium with said salt or complex ion is less than about $10^{-5}$M; and (f) detecting the formation of a solid salt or immobilized complex of said anion or polymeric anion and said cationic meriquinone, wherein said formation indicates the presence of the material.

31. A process for visualizing an analyte selected from the group consisting of an antigen, an antibody and a nucleic acid, contained in or on a solid phase using a Southern blot, a Northern blot, a DNA or RNA dot blot, a Western blot, an antigen dot blot or an antibody dot blot, which process comprises:

(a) contacting the solid phase with a detecting compound selected from the group consisting of (i) an antibody capable of binding to the antigen, (ii) an antigen or anti-antibody capable of binding to the antibody, or (iii) a nucleic acid hybridization probe containing a single-stranded nucleotide sequence which is complementary to a sequence contained in the nucleic acid;

(b) contacting the solid phase from step (a) with a peroxidase attached to a moiety capable of binding to the detecting compound;

(c) incubating the solid phase from step (b) under conditions whereby the detecting compound will bind to the peroxidase and to the antigen, antibody or nucleic acid if it is present in the solid phase;

(d) washing the solid phase from step (c) to remove unbound detecting compound and peroxidase;

(e) adding to the washed solid phase from step (d) a benzidine compound given by the structure

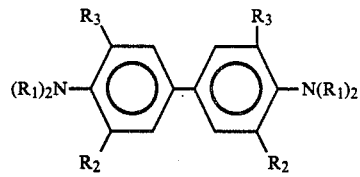

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, and wherein the concentration of dissolved meriquinone in equilibrium with said salt or complex ion is less than about $10^{-5}$M;

(f) subjecting the solid phase to conditions under which the benzidine compound will oxidize to the meriquinone thereof if the peroxidase is present, said conditions comprising a reaction temperature of 0° to 60° C. and an aqueous medium of pH 3 to 7 containing an amount of a hydroperoxide effective to oxidize the benzidine compound;

wherein an amount of an anion or polymeric anion effective to cause formation of a solid salt or immobilized complex of the anion or polymeric anion with the meriquinone is added during one or more of steps (a)–(f); and (g) detecting the formation of a solid salt or immobilized complex of said anion or polymeric anion and said cationic meriquinone, wherein said formation indicates the presence of the antigen, antibody or nucleic acid.

32. The process of claim 31 wherein the substituted benzidine is 3,3',5,5'-tetramethylbenzidine, the anion or polymeric anion is added to step (c), (d), or (e), and the hydroperoxide is hydrogen peroxide.

33. The process of claim 32 wherein the analyte is DNA, the detecting compound is a DNA hybridization probe labeled with biotin, the peroxidase is horseradish peroxidase conjugated to streptavidin, the anion or polymeric anion is citrate, fumarate, polyacrylate, polymethacrylate or dextran sulfate, and the process is used in a Southern blot.

34. The process of claim 33 wherein during step (c) or (d) a detergent and/or a urea is used as the incubation or washing solvent and/or during step (f) a cosolvent is employed selected from the group consisting of isopropyl alcohol, ethyl alcohol and dimethyl sulfoxide.

35. The process of claim 32 wherein the analyte is an antigen or antibody, the detecting compound is an antibody specific to the antigen to be detected or an antiantibody or antigen specific to the antibody to be detected, the peroxidase is horseradish peroxidase conjugated to an antigen, anti-antibody or antibody capable of specifically interacting with the detecting compound and the anion or polymeric anion is citrate, fumarate, polyacrylate, polymethacrylate, or dextran sulfate.

36. The process of claim 35 wherein the analyte is a ras p21 protein antigen, the detecting compound is an antibody directed to a specific mutant of said protein, and the horseradish peroxidase is conjugated to an anti-antibody specific to the detecting compound.

37. A process for detecting the presence of an analyte comprising an antigen or an antibody in a liquid test sample, which process comprises:
 (a) incubating the test sample or an extract thereof with a surface to capture the antigen or antibody and with a peroxidase-labeled antibody or antigen which binds to the antigen or antibody to be detected, these incubations occurring separately, in either order, or together;
 (b) filtering the incubation mixture of step (a);
 (c) washing the filter of step (b);
 (d) incubating the washed product of step (c) with a hydroperoxide and a benzidine compound given by the structure

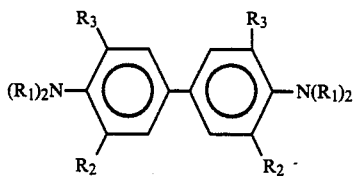

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, and an amount of an anion or polymeric anion effective to form a solid salt or immobilized complex with the meriquinone of said benzidine or substituted benzidine, and wherein the concentration of dissolved meriquinone in equilibrium with said salt or complex ion is less than about $10^{-5}$M;
 (e) filtering and washing the incubate of step (d); and
 (f) detecting the formation of said solid salt or immobilized complex of said anion or polymeric anion and the meriquinone of said benzidine compound, wherein said formation indicates the presence of said antibody or antigen.

38. The process of claim 37 wherein the surface to capture the antibody or antigen is a filter membrane or beads suspended in the test sample above a filter membrane, the benzidine compound is TMB, steps (d) and (e) are carried out at a low ionic strength and at a pH of 3.5–5.5, and the hydroperoxide is hydrogen peroxide.

39. A kit for detecting the presence of an analyte selected from the group consisting of an antigen, an antibody, and a nucleic acid, which kit includes instructions which result in the immobilization or precipitation of the meriquinone of a benzidine, the benzidine compound having the structure

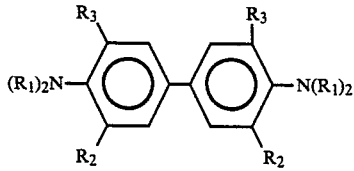

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, by application of a polymeric anion or a concentration of an anion sufficient to give a meriquinone solubility below $10^{-5}$M.

40. The kit of claim 39 further comprising an immobilizing or precipitating anion or polymeric anion.

41. The kit of claim 40 wherein the aniol is selected from the group consisting of maleate, oxalate, malonate, succinate, glutarate, fumarate, phthalate, isophthalate, terephthalate, malate, tartarate, pyrophosphate, formate, isocitrate, ethylenedinitrilotetra-acetate, 1,2,3,4-butane tetracarboxylate, benzoate, hemimellitate, trimellitate, trimesate, pyromellitate, mellitate and mesaconate.

42. The kit of claim 41, wherein the benzidine compound is TMB and the anion may also be a halide, nitrate, citrate, or sulfate.

43. The kit of claim 40, wherein the assay format is that of a Southern blot, Northern blot, nucleic acid dot blot, Western blot, immunodot blot, enzyme immunoassay, or solution-phase nucleic acid hybridization assay.

44. The kit of claim 43, wherein the DNA of the analyte is all or part of a gene from an HTLV III virus, all or part of an HLA gene, all or part of the gene for a normal or mutant hemoglobin, or all or part of an oncogene, and the format is that of a Southern blot, nucleic acid dot blot, or solution-phase nucleic acid hybridization assay.

45. The kit of claim 43, wherein the antigen is an oncogene product, and the assay format is that of a Western blot, immunodot blot, or enzyme immunoassay.

46. The kit of claim 43, wherein the antigen is human chorionic gonadotrophin or human lutenizing hormone, and the assay format is that of an immunodot blot or enzyme immunoassay.

47. The kit of claim 43, wherein the antigen is derived from the group of pathogenic organisms consisting of Neisseria gonorrhea, Chlamydia, or Herpes simplex virus, and the assay format is that of an immunodot blot or enzyme immunoassay.

48. The kit of claim 39, further comprising:
 (a) a detecting compound selected from the group consisting of: (i) an antibody capable of specifically binding to an antigen, (ii) an antibody or anti-antibody capable of specifically binding to an antibody, and (iii) a nucleic acid hybridization probe containing a single-stranded nucleotide sequence which is complementary to a sequence contained in the nucleic acid;
 (b) a conjugate of a peroxidase and a moiety capable of specifically binding to the detecting compound; and
 (c) a benzidine compound given by the structure

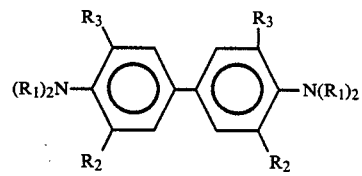

in which $R_1$ is H and $R_2$ and $R_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10.

49. The kit of claim 48 wherein the benzidine compound is TMB, the analyte is a ras p21 protein antigen, the detecting compound is an antibody directed to a specific mutant of said protein, and the horseradish peroxidase is conjugated to an anti-antibody specific for the detecting compound, and the kit is used in a Western blot.

50. The kit of claim 49 further comprising one of more controls.

51. The kit of claim 48 wherein the benzidine compound is TMB, the analyte is DNA, the detecting compound is a DNA hybridization probe labeled with biotin, the peroxidase is horseradish peroxidase conjugated to streptavidin, and the process used is a Southern blot.

52. The kit of claim 39 for detecting one or more antibodies or antigens in a test sample using an enzyme immunoassay format, which kit further comprises:
(a) a benzidine compound given by the structure

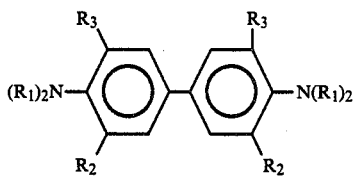

in which R$_1$ is H and R$_2$ and R$_3$ are independently selected from the group consisting of —H, —F, —Cl, —Br, —CH$_3$, —OCH$_3$, —(CH$_2$)$_n$CH$_3$, and —O—(CH$_2$)$_n$CH$_3$, where n is an integer of from 1 to 10, with the proviso that R$_1$, R$_2$ and R$_3$ are not all —H;
(b) a conjugate of a peroxidase to a compound which will detect said antigen or antibody; and either
(c) an incubation buffer containing an anion or polymeric anion which will precipitate the meriquinone of said benzidine compound; or
(d) a filter membrane or a trapping component bearing fixed negative charges selected from the group consisting of a filter membrane, latex beads, a dipstick, or a cation-exchange resin.

53. The kit of claim 52 further comprising one or more controls, where the benzidine compound is TMB, the anion is fumarate, and the peroxidase is horseradish peroxidase.

54. A composition of matter useful for visualization of oxidants, oxidation catalysts for peroxidative catalysts, comprising a complex of a polymeric anion and a meriquinone of a benzidine compound selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

55. A composition of matter useful for visualization of oxidants, oxidation catalysts, or peroxidative catalysts, comprising a solid salt of an anion and the meriquinone of a benzidine compound selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine, wherein the anion is selected to give a meriquinone solubility of less than about 10$^{-5}$M.

56. The composition of claim 4 wherein the meriquinone is of a benzidine compound selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

57. The composition of claim 5 wherein the meriquinone is of a benzidine compound selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

58. The process of claim 9 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

59. The process of claim 26 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

60. The process of claim 28 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

61. The process of claim 30 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

62. The process of claim 31 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

63. The process of claim 37 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

64. The kit of claim 39 wherein the benzidine compound is selected from the group consisting of benzidine, TMB, o-dianisidine, o-tolidine, 3,3'-diethylbenzidine, 3,3'-difluorobenzidine, 3,3'-dichlorobenzidine and 3,3'-dibromobenzidine.

65. The process of claim 23 wherein the solid phase comprises an ion exchange resin.

66. The process of claim 23 wherein said ion exchange resin comprises a material selected from the group consisting of carboxymethyl cellulose, carboxymethyl Sepharose, sulfopropyl Trisacryl, diethylaminoethyl cellulose and diethylaminoethyl Sepharose.

67. The process of claim 37, wherein
(1) more than one antigen or antibody are analytes and are captured in step (a) if present in the test sample;
(2) the surface to capture said analytes is a filter membrane or beads suspended in an aqueous medium above a filter membrane;
(3) the peroxidase-labeled antibody or antigen in step (a) binds specifically to only one of the analytes; and
(4) the following additional steps are taken after step (f):
(g) washing the filter of step (e) with an amount of aqueous solvent of ionic strength above about 0.1 effective to dissolve the meriquinone contained in said solid salt or immobilized complex;
(h) incubating said surface-captured analytes with a peroxidase-labeled antibody or antigen which binds to a different analyte from that detected in step (a);
(i) repeating steps (b)–(f); and, optionally,
(j) repeating steps (g)–(i) using in each repetition a peroxidase-labeled antibody or antigen which binds to a different analyte than detected in a previous step, until all analytes have been found to be present or absent in the test sample.

* * * * *

UNITED STATES PATENT AND TRADEMARK OFFICE
CERTIFICATE OF CORRECTION

PATENT NO. : 4,789,630　　　　　　　　　　　　　　　　　　　Page 1 of 2

DATED : December 6, 1988

INVENTOR(S) : Will Bloch, Patrick J. Sheridan, Robert J. Goodson

It is certified that error appears in the above-identified patent and that said Letters Patent is hereby corrected as shown below:

```
Title page [75] add H. Garrett Wada as a co-inventor on the patent.
Column 1, line 28, change "tion" to --tions--.
Column 1, line 67, change "occuring" to --occurring--.
Column 3, line 13, change "of liability" to --or lability--.
Column 5, line 9, change "polymorphic" to --polymeric--.
Column 14, line 29, change "carboxylate" to --carboxylic--.
Column 15, line 19, change "the" to --and--.
Column 15, line 35, change "etyl" to --ethyl--.
Column 17, line 61, change "fluocarbon" to --fluorocarbon--.
Column 18, line 50, change "peroxide" to --peroxidase--.
Column 21, line 15, change "leulocyte" to --leukocyte--.
Column 22, line 21, change "as" to --at--.
Column 22, line 28, change "latitute" to --latitude--.
Column 22, line 45, change "crystal" to --crystals--.
Column 23, line 12, change "terminatng" to --terminating--.
Column 26, line 33, change "correspnding" to --corresponding--.
Column 27, line 25, change "sultate" to -sulfate--.
Column 27, line 26, between "any" and "close" insert --pH--.
Column 29, line 57, change "acatate" to --acetate--.
Column 29, line 61, change "polyacrylwate to --polyacrylate--.
Column 31, line 43, change "develloped" to --developed--.
Column 32, line 3, change "should" to --could--.
Column 37, line 67, change "p21. to --p21,--.
```

UNITED STATES PATENT AND TRADEMARK OFFICE
CERTIFICATE OF CORRECTION

PATENT NO. : 4,789,630

DATED : December 6, 1988

INVENTOR(S) : Will Bloch, Patrick J. Sheridan, Robert J. Goodson

It is certified that error appears in the above-identified patent and that said Letters Patent is hereby corrected as shown below:

Column 39, line 6, change "$10^{31}$ $^{17}$" to --$10^{-17}$--.
Column 39, line 51, change "Trans-" to --Tran---.
Column 39, line 54, change "100)1" to --100 ul--.
Column 39, line 67, change "25)1" to --25 ul--.
Column 39, line 68, change "20)1" to --20 ul--.
Column 40, line 5, change "800-850)1" to --800-850 ul--.
Column 41, line 10, change "g-globin" to --b-globin--.
Claim 26, column 45, line 33, before "analyte" insert --bind to the --.
Column 27, move lines 57-58 to immediately after the end of Table II.
Column 39, Table V, line 54, change "$WA_{652}S^{-1}$" to --$\Delta A_{652}S^{-1}$--

Claim 26, column 45, line 21, after "analyte" insert --is--.
Claim 48, column 50, line 43, change "antibody" to --antigen--.
Claim 57, column 51, line 66, change "claim 5" to --claim 2--.

Signed and Sealed this

Twelfth Day of December, 1989

Attest:

JEFFREY M. SAMUELS

*Attesting Officer*    Acting Commissioner of Patents and Trademarks